United States Patent
O'Young et al.

(10) Patent No.: US 6,610,891 B1
(45) Date of Patent: Aug. 26, 2003

(54) METHOD OF PRODUCING ALDEHYDES

(75) Inventors: Lionel O'Young, Redwood City, CA (US); Masaki Takai, Yokohama (JP); Tooru Tsukahara, Kurashiki (JP); Akio Nakanishi, Kurashiki (JP)

(73) Assignee: Mitsubishi Chemical Corporation, Tokyo (JP)

( * ) Notice: Subject to any disclaimer, the term of this patent is extended or adjusted under 35 U.S.C. 154(b) by 0 days.

(21) Appl. No.: 09/454,817

(22) Filed: Dec. 3, 1999

(51) Int. Cl.⁷ ............................ C07C 45/49; B01J 31/00
(52) U.S. Cl. ................ 568/451; 568/454; 502/158
(58) Field of Search ................ 568/451, 454; 502/158

(56) References Cited

U.S. PATENT DOCUMENTS

| | | | |
|---|---|---|---|
| 4,599,206 A | 7/1986 | Billig et al. | 558/85 |
| 4,668,651 A | 5/1987 | Billig et al. | 502/158 |
| 4,748,261 A | 5/1988 | Billig et al. | 556/404 |
| 4,885,401 A | 12/1989 | Billig et al. | 568/454 |
| 5,059,710 A | 10/1991 | Abatjoglou et al. | 558/78 |
| 5,113,022 A | 5/1992 | Abatjoglou et al. | 568/454 |
| 5,288,918 A | 2/1994 | Maher et al. | 568/454 |
| 5,648,553 A | 7/1997 | Ueda et al. | 568/454 |
| 5,648,554 A | 7/1997 | Mori et al. | 568/454 |
| 5,663,403 A | 9/1997 | Sato et al. | 558/156 |
| 5,672,766 A | 9/1997 | Mori et al. | 568/454 |
| 5,728,861 A | 3/1998 | Sato et al. | 568/454 |
| 5,807,763 A | 9/1998 | Motika et al. | 438/18 |
| 5,865,957 A | 2/1999 | Ueda et al. | 203/25 |
| 5,910,600 A | 6/1999 | Urata et al. | 558/162 |
| 5,936,130 A | 8/1999 | Mori et al. | 568/454 |

*Primary Examiner*—Johann Richter
*Assistant Examiner*—Sikarl A. Witherspoon
(74) *Attorney, Agent, or Firm*—Dorsey & Whitney LLP

(57) ABSTRACT

A method of producing aldehydes in a hydroformylation system wherein an olefinic compound is reacted with hydrogen and carbon monoxide in a hydroformylation reaction in the presence of a catalyst is provided. The hydroformylation system includes a reactor and a downstream catalyst process path. The temperature in the reactor and downstream catalyst process path is less than approximately 100° C., and preferably less than approximately 85° C., and most preferably less than approximately 80° C., such that formation of high boiler components from the reaction are substantially minimized. Further, the method of the present invention reduces degradation or decomposition of the catalyst, and in particular the ligand compound.

30 Claims, 2 Drawing Sheets

METHOD OF PRODUCING ALDEHYDES

FIELD OF THE INVENTION

The present invention relates generally to a method of producing aldehydes. More particularly, the present invention relates to a method of producing aldehydes using a hydroformylation reaction wherein the formation of high boiling point components and decomposition of the catalysts, and in particular the ligand are minimized. The aldehydes produced may be an end product, or alternatively may be an intermediate product employed in further processing.

BACKGROUND OF THE INVENTION

The production of aldehydes is an important process in the chemical industry. Aldehydes are widely used for a variety of purposes, for example as a precursor for the formation of 2-ethyhexanol (2EH) which is an important raw material for plasticizer, or upon subsequent hydrogenation to form alcohols. Aldehydes may be produced by a variety of methods. One important production method is hydroformylation. The hydroformylation reaction basically combines an alkene with carbon monoxide and hydrogen, in the presence of a catalyst, to form an aldehyde of one carbon number higher than the feed alkene. For example, the hydroformylation of propylene forms butyraldehydes, also referred to as C4 aldehydes. Examples of some prior art hydroformylation processes are described in U.S. Pat. Nos. 4,599,206; 4,748,261; 4,885,401; 5,059,710; 5,288,918; 5,648,553; 5,663,403; and 5,672,766.

In general the prior art hydroformylation systems typically involved the production of aldehydes, and optionally alcohols by further hydrogenation of the aldehydes, by reacting an olefinic compound with hydrogen and carbon monoxide in the presence of a catalyst, most often a metal organophosphorus ligand compound catalyst. A solvent may be employed to dissolve and disperse the reactants in solution thereby providing a reaction solution. The prior art systems are typically a liquid recycle system, that is at least a portion of the reaction solution is withdrawn from the hydroformylation reactor containing aldehyde products along with remaining reactants and catalyst either continuously or periodically. The aldehyde products, and optionally one or more of the reactants and catalyst, are separated in what is generally termed a separation system. The separation system includes a downstream catalyst process path, which is the path the catalyst is exposed to during separation and/or recovery from the reaction solution. FIG. 1 is one illustrative example of such a prior art hydroformylation system. In FIG. 1 the reactor is designated as numeral 10 and the separation system is generally designated as numeral 12. Generally, the reactor 10 includes a continuous stirred tank reactor (CSTR). Optionally, additional equipment may be employed as part of the reactor 10 to increase the conversion of the olefinic compound to aldehydes. To produce C4 aldehydes, feed propylene (PPY) is conveyed via first inlet means to the reactor 10. Hydrogen ($H_2$) and carbon monoxide (CO), often supplied as a gas mixture, better known as oxo gas or synthesis gas are typically introduced via a second inlet means to the hydroformylation reactor 10 or its associated additional equipment. Generally, the $H_2$ and CO concentration in the oxo gas is about 1:1 molar ratio. The main controlling limitation for the overall propylene conversion is the purity of the propylene or synthesis gas feed stream. If the feed stream is of low purity, then the overall conversion of propylene to C4 aldehydes becomes lower. In the instance where the low purity propylene or synthesis gas is used with its low conversion, additional equipment suitably adapted to provide further conversion of the propylene or synthesis gas may be employed. Thus, while the reactor 10 is shown simply as a block in FIG. 1 the reactor may include various unit operations commonly employed in conventional hydroformylation reactor systems.

The aldehyde products are generally separated and recovered from the reaction solution in the separation system 12. Many types of separation systems 12 are utilized in the prior art hydroformylation systems. For example the aldehyde products may be separated and/or recovered from the hydroformylation reaction solution by composite membrane techniques, or optionally by the more commonly used vaporization separation techniques of distillation, such as single or multiple stage distillation under reduced, normal or high pressures, as applicable in an aldehyde removal unit 14. Condensation of the volatilized materials and separation and further recovery thereof may be carried out by conventional means, and the remaining reactants and optionally additionally the solvents contained within the reaction solution may be separated in solvent recovery unit 16 and recycled back to the hydroformylation reactor. Such types of continuous hydroformylation systems are well known in the art and thus need not be described in further detail here. Examples of such continuous prior art systems can be found in U.S. Pat. Nos. 5,087,763 and 5,865,957.

These continuous hydroformylation systems suffer from the build-up of detrimental by-products. Specifically, during the hydroformylation process, other reactions occur in addition to the formation of aldehydes. Many higher boiling point components such as dimers, trimers, tetramers of aldehydes and the like are formed as a by product of the reaction. These high boiling point by-product components (hereinafter referred to as "high boilers") are detrimental to the process and severely reduce the aldehyde yield. Thus, in the prior art systems it is necessary to remove them from the hydroformylation reactor effluent stream. The high boilers are removed in a variety of conventional techniques, such as by employing one or more a high boiler separation units, such as that described in U.S. Pat. No. 5,648,554, where vaporization or distillation in one or more stages distillation under normal, reduced or elevated pressures is used. Thus, it is highly desirable to provide a method wherein the formation of high boilers are reduced and/or minimized.

An important aspect of the hydroformylation process is the catalyst utilized to assist the hydroformylation reaction. It is common to use a soluble complex of an element selected from Groups VIII to X of the Periodic Table (hereinafter referred to as a "Group VIII metal") having an organic phosphorus compound as a ligand. In general, the ligand used together with the metal component of the catalyst gives substantial influence to the catalytic reaction. Rhodium (Rh) is commonly used as the metal component of the catalyst. Rh will form a complex molecule with the ligand which activates the hydroformylation reaction. Significant effort has been focused on the development of catalysts as demonstrated by U.S. Pat. Nos. 4,668,651, 5,113,022, 5,663,403, 5,728,861, among others. Unfortunately, however, this complex molecule decomposes during the reaction at a significantly high rate such that the spent or deactivated catalyst must be removed from the reactor and replaced with new, activated catalyst. In prior art systems the catalyst may be removed by conveying the catalyst via a downstream catalyst process path into the separation system 12, such as by employing a split stream from the bottom of the high boilers separation unit 18 and conveyed to suitably configured catalyst removal unit 20. For example, U.S. Pat. Nos. 4,668,651 and 5,113,022 describe a process where the liquid reaction solution is passed to a vaporizer/separator where the aldehyde product is removed via distillation in one or more states under normal, reduced or elevated pressure, and it is preferred to separation the desired aldehyde produce from the rhodium catalyst solution under reduced pressure at temperatures below 150° C. and preferably below 130° C. While the aldehyde product is separated in such process, the inventors have found that much of the catalyst degrades at these relatively high temperatures. Since significant effort and expense is taken to recover the catalyst and particularly the ligand compound, it is desirable and would be a significant advance in the art to provide a hydroformylation method that minimizes the degradation of the catalyst/ligand compound.

OBJECTS AND SUMMARY OF THE INVENTION

Accordingly, it is an object of the present invention to provide an improved method of producing aldehydes.

More particularly, it is an object of the present invention to provide a method of producing aldehydes using a hydroformylation reaction where the formation of high boilers are minimized.

Another object of the present invention is to provide a method of producing aldehydes by hydroformylation where degradation and/or decomposition of the catalyst, and in particular the ligand compound used in the reaction is minimized.

A further object of the present invention is to provide a method of producing aldehydes employing a low boiling point solvent, such as an aldehyde.

A related object of the present invention is to provide a method of producing aldehydes which reduces the operating cost of the production and reduces the number of unit operations needed to carry out the process thereby further reducing the operating and maintenance costs.

These and other objects and advantages of the present invention are achieved by a method of producing aldehydes wherein an olefinic compound is reacted with hydrogen and carbon monoxide in a hydroformylation reaction in the presence of a catalyst. The hydroformylation system comprising the hydroformylation reaction, and optionally additionally a downstream catalyst process path and/or separation steps, is carried out at a temperature of less than approximately 100° C., and preferably less than approximately 85° C., and most preferably less than approximately 80° C., such that formation of high boilers during the hydroformylation reaction and decomposition of the catalyst are substantially minimized.

In another embodiment of the present invention a method of producing aldehydes is provided wherein an olefinic compound is reacted with hydrogen and carbon monoxide in a hydroformylation reaction in the presence of a catalyst. There is no real limitation to the activity of the catalyst, but for economic considerations it is preferred that the catalyst be selected such that it exhibits a reaction half time of approximately one hour or less at the selected reaction temperature and pressure. The hydroformylation reaction, and optionally additionally the downstream catalyst process path and/or the separation steps, is carried out at a temperature of less than approximately 100° C., and preferably less than approximately 85° C., and most preferably less than approximately 80° C., wherein formation of high boilers and degradation of the catalyst, in particular the ligand, are substantially minimized.

In yet another embodiment of the present invention a method of producing aldehydes is provided wherein an olefinic compound is reacted with hydrogen and carbon monoxide in a hydroformylation reaction in the presence of a catalyst. The hydroformylation reaction, and optionally additionally the downstream catalyst process path and/or the separation steps, is carried out at a temperature of less than approximately 100° C., and preferably less than approximately 85° C., and most preferably less than approximately 80° C., such that formation of high boilers and decomposition of the catalyst are substantially-minimized, and where the catalyst includes phosphite compounds which may be used in the method of the present invention. These phosphite compounds include, but are not particularly limited to, triaryl phosphites, trialkyl phosphites, arylalkyl phosphites, or any other phosphite. Bisphosphite and polyphosphite compounds or the like which have combinations of these in the same molecule are also included.

More specifically, monophosphite compounds can be divided into the two following compound groups. That is, one group of compounds comprises phosphite compounds having a cyclic structure, with phosphorus atoms contained in the cyclic structure. The other group of compounds comprises phosphite compounds that have no cyclic structure containing phosphorus atoms.

Among monophosphite compounds which can be used in the hydroformylation reaction encompassed in the present invention, those phosphite compounds represented by the following formula are preferred among the latter compounds, that is, phosphite compounds that have no cyclic structure containing phosphorus atoms.

$$P(OR1)(OR2)(OR3) \qquad (1)$$

Where R1, R2, and R3 are optionally $C_1$ to $C_{30}$ substituent-bearing alkyl groups, cycloalkyl groups, aryl groups, aralkyl groups, and heteroaryl groups. Examples of substituents are not particularly limited, provided that they do not inhibit the reaction, and include $C_1$ to $C_{20}$ alkyl groups, cycloalkyl groups, alkoxy groups, halogens, alkylamino groups, acyl groups, carboalkoxy groups, and hydroxycarbonyl groups.

Desirable compounds among these are organic phosphite compounds in which at least one of R1, R2, or R3 in General Formula 1 is a substituted aryl group represented by General Formula 2:

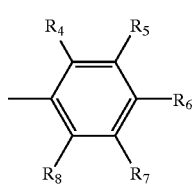

(2)

where R4 is —C(R9)(R10) R11 or an optionally substituted aryl group; R9, R10, and R11 are each independently a hydrogen atom, fluorohydrocarbon group or hydrocarbon group; R4 preferably has steric hindrance as a whole equal to or greater than isopropyl groups; and R5, R6, R7, and R8 are each independently a hydrogen atom or organic group, and may also be condensed aromatic rings or hetero rings with adjacent substituents such as R6 and R7 bonded to each other.

Other monophosphite compounds which can be used in the reaction encompassed in the present invention include phosphite compounds represented by the following General Formula 3, which are phosphite compounds of the other group of compounds that have a cyclic structure, with phosphorus atoms contained in the cyclic structure.

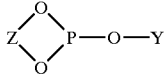

(3)

Where Z is a divalent organic group, and Y is an optionally substituted monovalent organic group.

Examples of bisphosphite and polyphosphite ligands which can be used in the reaction encompassed in the present invention include compounds represented by General Formula 9.

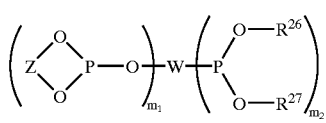

(9)

Where Z represents the same divalent organic groups as those defined in General Formula 3 above; and R26 and R27 are each independently optionally $C_1$ to $C_{30}$ substituent-bearing alkyl groups, cycloalky groups, aryl groups, aralkyl groups, and hereroaryl groups. Examples of substituents are not particularly limited, provided they do not inhibit the reaction, and include $C_1$ to $C_{20}$ alkyl groups, cycloalkyl groups, alkoxy groups, halogens, alkylamino groups, acyl groups, acyloxy groups, and arkoxycarbonyl groups. Examples of end organic groups represented by R26 and R27 include $C_1$ to $C_{20}$ straight-chain or branched alkyl groups such as methyl, ethyl, n-propyl, isopropyl, n-butyl, s-butyl, t-butyl, n-pentyl, isopentyl, neopentyl, t-pentyl, and t-hexyl; $C_3$ to $C_{20}$ cycloalkyl groups such as cyclopropyl, cyclohexyl, cyclooctyl, and adamantyl; optionally substituent-bearing aryl groups such as phenyl, α-naphthyl, β-naphthyl, methoxyphenyl, dimethoxyphenyl, methoxycarbonylphenyl, cyanophenyl, nitrophenyl, chlorophenyl, dichlorophenyl, pentafluorophenyl, methylphenyl, ethylphenyl, dimethoxyphenyl, trifuoromethylphenyl, methylnaphthyl, methoxynaphthyl, chloronaphthyl, nitronaphthyl, and tetrahydronaphthyl; aralkyl groups such as benzyl; and heterocyclic aromatic groups such as pyridyl, methylpyridyl, nitropyridyl, pyrazyl, pyrimidyl, benzofuryl, quinolyl, isoquinolyl, benzimidazolyl, and indolyl. W is an optionally substituted m-valent hydrocarbon group, m1 and m2 are each independently an integer of 0 to 6, where m=m1+m2 has a value of 2 to 6. When m1 and m2 are each more than 2, then Z, R26 and R27 may be the same as or different from each other.

Even more desirable compounds include those in which Z in General Formula 9 is Z defined in General Formula 6 above, and compounds in which W is represented by General Formula 10.

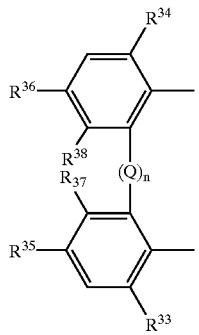

(10)

where R37 and R38 are each independently a $C_1$ to $C_{12}$ alkyl group, cycloalkyl group, alkoxy group, silyl group, siloxy group, or a halogen atom or hydrogen atom. Examples include hydrogen atoms, or methyl, ethyl, n-proply, isopropyl, n-butyl, methoxy, ethoxy, and n-propoxy groups, and fluorine, chlorine, bromine, or iodine atoms. R33 through R36 are each independently a $C_1$ to $C_{20}$ alkyl, cycloalkyl, alkoxy, silyl, or siloxy group, or a halogen or hydrogen atom. Examples include hydrogen, methyl, ethyl, n-propyl, isopropyl, n-butyl, t-butyl, t-pentyl, neopentyl, t-hexyl, nonyl, decyl, methoxy, ethoxy, and t-butoxy groups. Specific examples of Formula 10 include those in which R35 and R37 and/or R36 are R38 each independently bond to each other to form part of a cyclic structure consisting of 3 to 40 carbons. A specific example is 1,1-binaphthyl-2,2'-diyl. Further description is provided below in the detailed description of the invention.

In an even further embodiment of the present invention a method of producing aldehydes is provided wherein an olefinic compound is reacted with hydrogen and carbon monoxide in a hydroformylation reaction. A solvent is suitably added to assist in the hydroformylation reaction and the solvent is selected such that it exhibits a low boiling point which is defined as a boiling point that is equal to or greater than the boiling point of the aldehydes products. In one embodiment, the solvent is selected such that it is comprised, at least partially, of one or more aldehydes and/or alcohols such as an aldehyde or alcohol reactant, or optionally any of the aldehydes and/or alcohols formed in the hydroformylation reaction.

BRIEF DESCRIPTION OF THE DRAWINGS

Additional objects and advantages of the invention will become apparent in reading the detailed description of the invention and the claims and with reference to the figures, in which:

DETAILED DESCRIPTION OF THE INVENTION

Figure 1:
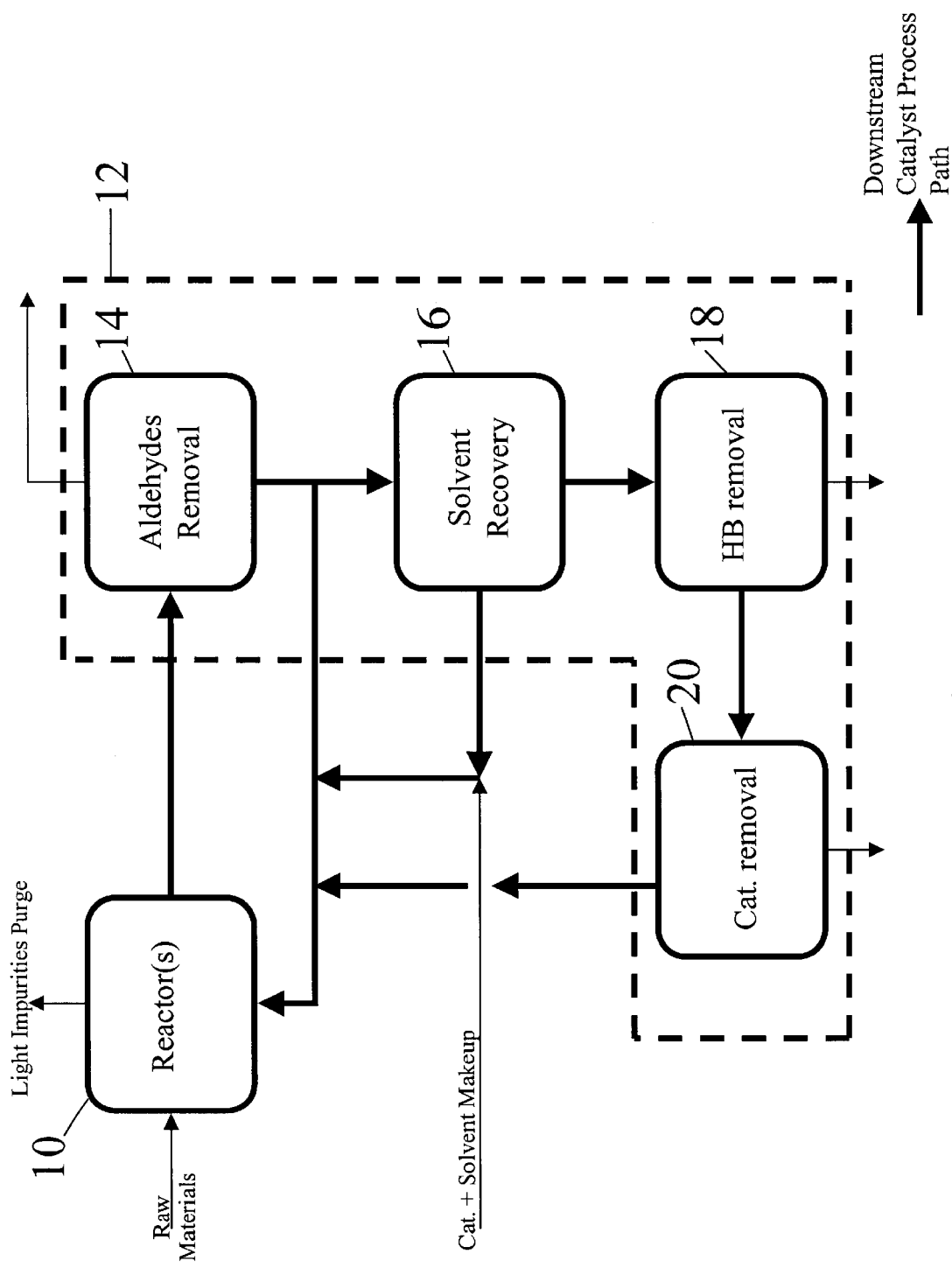
FIG. 1 is a schematic diagram of a prior art hydroformylation system.

The present invention is directed to a method of producing aldehydes wherein an olefinic compound is reacted with hydrogen and carbon monoxide in a hydroformylation reaction in the presence of a catalyst. The aldehydes produced according to the method of the present invention may be employed as an end product, or alternatively may be employed as an intermediate product which is then employed in further processing to obtain other desired end products. After substantial study and effort, the inventors have discovered that by employing a low temperature, specifically wherein the hydroformylation reaction, and optionally additionally the downstream catalyst process path and/or the separation steps, is carried out at a temperature of less than approximately 100° C., preferably less than approximately 85° C., more preferably less than approximately 80° C., with a range of about 45° C. to 70° C. being most preferred for the hydroformylation reaction, and a range of about 40° C. to 80° C. being most preferred for the downstream catalyst process path and separation steps, the formation of high boilers and decomposition of the catalyst are substantially minimized, thereby affording a great advantage as a method of producing aldehydes. Of further significant advantage among others, this low temperature employed in the downstream catalyst process path increases the stability of the catalyst and minimizes the catalyst, and in particular the ligand, degradation or decomposition throughout the entire hydroformylation system. As will be described in detail below, in addition to the aforementioned advantages, the present invention further promotes the significant simplification of the hydroformylation processes and systems which enable significant cost savings, both in capital expenditures and operating costs, and realizes all efficiencies therewith.

Of significant advantage, the present invention provides for carrying out the hydroformylation reaction, and the downstream catalyst process path and/or the separation steps at a temperature of less than approximately 100° C., preferably less than approximately 85° C., more preferably less than approximately 80° C., with a range of about 45° C. to 70° C. being most preferred for the hydroformylation reactor and with a range of about 40° C. to 80° C. being most preferred for the downstream catalyst process path and separation steps. It is not necessary that the downstream catalyst process path and/or separation steps, and the hydroformylation reaction be carried out at the same temperature. Each of such systems may be carried out independently at different and/or distinct temperatures. Prior art systems typically operate at temperatures of 100° C. and above and are subject to the formation of large amounts of high boilers in both the hydroformylation reaction and in the attendant separation systems and downstream catalyst process path. Indeed the prior art downstream catalyst process path and separation systems often reach quite high temperatures, such as temperatures of 130° C. and greater. In contrast, after significant study and experimentation, the inventors have discovered that when the operating temperature of the hydroformylation reaction and the downstream catalyst process path in the separation system are maintained at lower temperatures, the formation of high boilers are significantly reduced. Further, the lower operating temperature in the hydroformylation reactor, and downstream catalyst process path (i.e. areas in which the catalyst is present), reduces degradation and/or decomposition of the catalyst, and in particular the ligand compound of the catalyst.

According to the present invention, the downstream catalyst process path is defined in the following manner. The downstream catalyst process path is the path the catalyst travels throughout the hydroformylation system downstream of the reactor. In other words, the downstream catalyst process path is anywhere the catalyst exists downstream of the reactor, and generally will include the recycle path from and back to the reactor. According to the present invention, the downstream catalyst process path passes through a portion, or alternatively all, of the units in the separation system. The downstream catalyst process path will vary depending on the type of design and system configuration used. For example, in the prior art system illustrated in FIG. 1, the downstream catalyst process path (shown by bold lines in FIG. 1) is defined by the path through the aldehyde removal unit 14, the solvent recovery unit 16, the high boilers separation unit 18 and the catalyst removal unit 20, in other words the whole separation system 12, since the catalyst passes through each one of these units.

Figure 2:
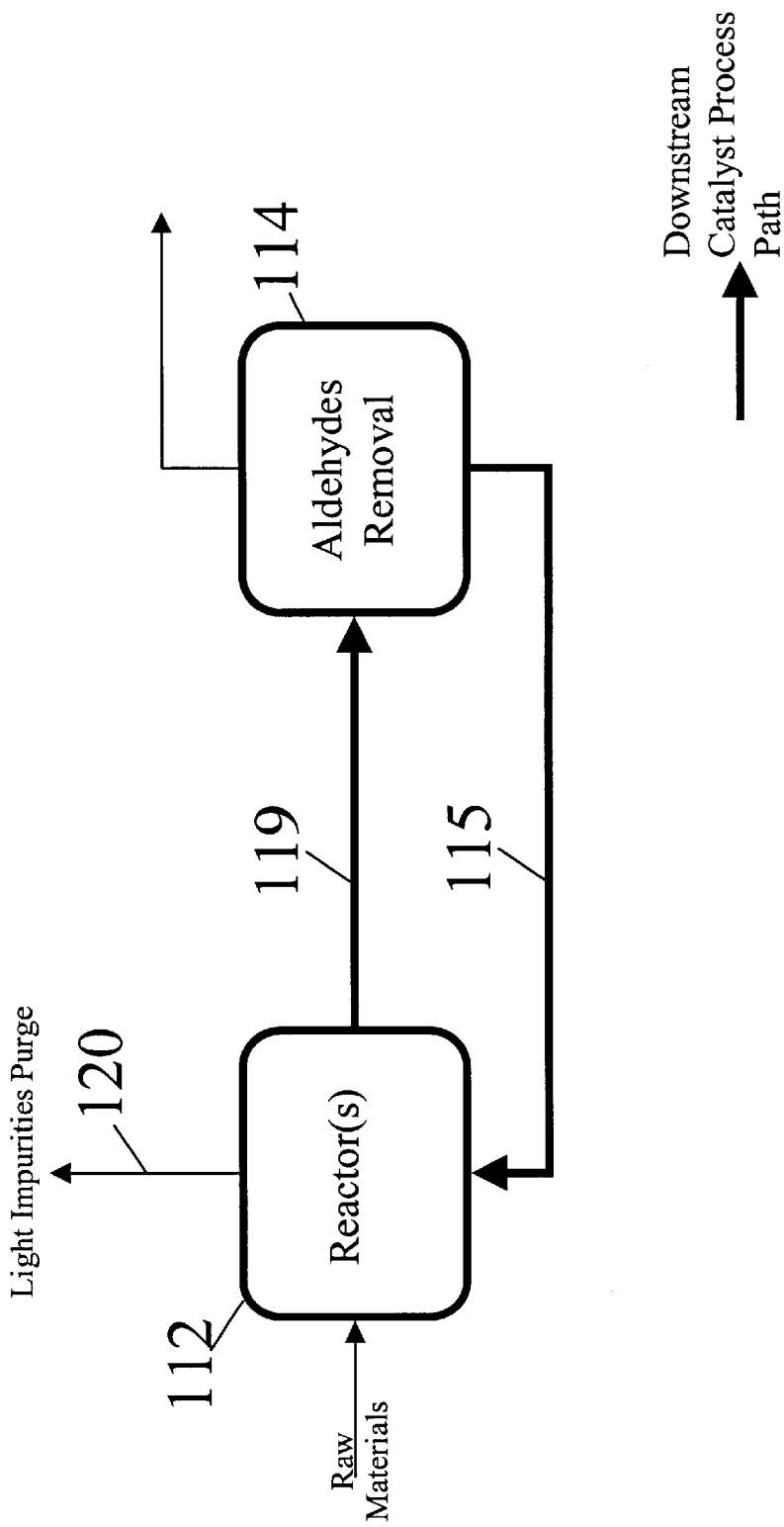
FIG. 2 is a schematic diagram of a hydroformylation system which may be carried out according to one embodiment of the present invention.

Alternatively, as shown in FIG. 2, according to the present invention, the catalyst passes downstream of the reactor through the stream 119 and the aldehyde removal unit 114 and is recycled back to the reactor 112 via recycle stream 115. Thus, the downstream catalyst process path is defined by the path through the stream 119, the aldehyde removal unit 114 and recycle stream 115 (as shown by bold lines in FIG. 2). Accordingly, as will be apparent to those of ordinary skill in the art, according to the present invention the downstream catalyst process path may be defined by a variety of different paths, but in all instances is defined as the path the catalyst travels downstream of the reactor within the hydroformylation system.

As heretofore mentioned, high boiler components are formed as a by-product of the hydroformylation reaction. Specifically, high boilers are formed primarily by side reactions of the aldehyde products formed in the hydroformylation reaction. Such side reactions additionally occur throughout the separation systems. For example, in a hydroformylation reaction of propylene, straight chain n-butyraldehyde and branched chain iso-butyraldehyde will be formed. These aldehyde products are highly reactive and tend to undergo polymerization or condensation slowly in the presence of the catalyst to form high boilers. Representative types of these high boilers from butyraldehyde include: dimers, trimers, tetramers, etc. as its self polymerization; 2-ethylhexenal as a condensed dimer, 2-ethylhexanal and 2-ethylhexanol as its hydrogenation products, among others. These high boilers are detrimental to the hydroformylation process and can severely reduce the n-butyraldehyde yield.

In the prior art techniques, significant efforts have been expended in the removal of such high boilers. The high boilers cause the boiling point of the catalyst solution to increase and must be removed, at least partially, over time as their concentration builds. Distillation is commonly used to withdraw the high boilers, however it is problematic because the catalyst is also subject to removal during distillation. The present invention advantageously eliminates these problems and expenses by minimizing the formation of the high boilers to a level suitable such that the high boilers do not require removal over a long period of time.

The formation of high boilers is a strong function of the temperature of the hydroformylation reaction, and of the temperature in the various separation steps and/or processes, employed. In the prior art systems, the high boilers are formed in the hydroformylation reactor as well as outside of the reactor in the various separation systems such as at the reboiler of the column for aldehyde removal, and at the reboiler of the solvent recovery column. The method of the present invention significantly reduces the formation of the high boilers. In particular, the method of the present invention provides for reducing the high boilers to a yield below 2 percent of the olefinic compound (in this case propylene) in the reactor, and more preferably to a yield of approximately 1.0 percent and below, and most preferably to a yield of approximately 0.10 percent and below.

Any number of suitable mechanical temperature controlling means may be employed with the method of the present invention to achieve the advantageous temperature of the hydroformylation reactor, and the downstream catalyst process path and any variety of separation systems employed. Hence, the manner and/or equipment employed to provide the suitable operational temperature is not limited, and its application need only be that minimum amount needed to provide the recited temperatures. By way of example and not by way of limitation, illustrative representative examples include the use of heat exchangers. Additional representative examples include the use of coolers or chillers, which may be employed to achieve the suitable temperature of the hydroformylation reaction, and optionally additionally the downstream catalyst process path and the separation system. Further illustrative specific examples include any variety and/or combination of equipment units which act to lower and/or maintain a certain temperature are suitable. In the preferred illustrative embodiment, the temperature of the hydroformylation system is maintained at less than approximately 100° C., preferably less than approximately 85° C., more preferably less than approximately 80° C. Most preferably, the hydroformylation reaction within the hydroformylation system is carried out at a temperature in the range of approximately 45° C. to 70° C., and the downstream catalyst process path and separation system within the hydroformylation system is carried out at a temperature in the range of approximately 40° C. to 80° C.

In another aspect of the present invention, the temperature of the hydroformylation system of the present invention may be achieved by other means, or by a combination of means. For example, the temperature of the hydroformylation reaction, and the downstream catalyst process path and/or separation system according to the present invention may be obtained in part by employing a solvent having a low boiling point. Alternatively, a combination of means may be used, such as employing the mechanical temperature controlling means along with a low boiling point solvent. When employing a low boiling point solvent, the type of solvent is not limited and the only criteria it preferably satisfies is to exhibit a low boiling point at the operational pressure of the hydroformylation reaction, and optionally additionally at the operational pressure of the separation system.

Accordingly, in the preferred embodiment, the present invention provides for the use of a solvent which exhibits a low boiling point. Preferably, the solvent will exhibit a normal boiling point that is equal to or greater than the boiling point of the aldehyde product. In the preferred case the solvent is the aldehyde itself, consequently there is no separation requirement, thereby providing for lower energy input to the hydroformylation system. This allows for relatively easy separation of the aldehyde products from the reaction mixture with relatively low energy input. A solvent having a normal boiling point of equal to or less than approximately 100° C. is most preferred. While the selection of a low boiling point solvent employed in the hydroformylation method of the present invention is preferred, the present invention is in no way limited by this selection, and the method of this invention may be carried out with any of the known solvents heretofore employed in conventional methods. Illustrative preferred embodiments include a solvent having a boiling point equal to or greater than the products formed in the hydroformylation reaction, with a boiling point of said solvent of equal to or less than approximately 100° C. being most preferred. In the preferred case, when the solvent is the aldehyde itself, it is most preferred when producing C4 aldehydes that the aldehyde solvent be substantially n-butyraldehyde; however, the aldehyde solvent can also be a mixture of n-butyraldehyde, iso-butyraldehyde, n-butyralcohol and iso-butyralcohol, or a mixture of any one of the same, which are also formed during the hydroformylation reaction.

Illustrated preferred embodiments of the solvent include employing aldehydes, or the hydroformylation reaction product as the solvent. More specifically, the hydroformylation reaction products, i.e. the aldehyde and/or alcohols produced from the hydroformylation reaction, exhibit a lower boiling temperature than conventional solvents, and thus by employing such hydroformylation reaction products as the solvent for the hydroformylation system, the operating temperature of the entire system is reduced as compared to systems employing conventional solvents. The aldehydes and/or alcohols employed as a solvent may be supplied as an initial charge to the starting materials. Of course, other representative embodiments are useful, for example where equipment may also be employed to lower the operating temperature alternatively, or in addition to using a low boiling point solvent. Theoretically, the operating temperature of the hydroformylation reaction, and optionally additionally the downstream catalyst process path and separation system, can be lowered to any value; however, there is a practical lower limit to the operating temperature at which the hydroformylation reaction rate will become too slow to produce products in an economical fashion, and heat removal will be too expensive. Accordingly, it is preferred that the operating temperature be no lower than about 35° C. to 40° C.

An illustrative preferred solvent of the present invention employs, at least partially and optionally substantially, an aldehyde or an alcohol as the solvent, and preferably one or more of the aldehyde products produced in the hydroformylation reaction. Specifically, the inventors have discovered that a solvent comprised, at least partially and optionally substantially, of one or more of the aldehyde products produced in the hydroformylation reaction is advantageous to the method. First, the aldehyde solvent exhibits a lower boiling point than conventional solvents which promotes operation of both the hydroformylation reaction and downstream catalyst process path in the advantageous temperature range of the present invention. Second, as discussed above, the prior art methods and systems have devoted great effort to the separation and removal of solvents from the aldehyde products and hydroformylation reaction solution. When a conventional solvent such as toluene is employed, for example in FIG. 1, the separation system would be suitably equipped with a toluene column necessary for the separation of toluene from the aldehyde products and/or hydroformylation reaction solution. By using one or more aldehydes, and optionally one or more of the aldehyde products as the solvent, the solvent separation system and/or process with all of its associated capital equipment and expense is substantially eliminated. In an alternative embodiment, the solvent is comprised at least partially of one or more aldehydes, and further comprised of any one of the following compounds as the balance: high boilers, aromatic hydrocarbons, ketones, ethers, esters, the olefinic starting material and any combination thereof. In this instance the solvent separation system is not necessarily eliminated but may be substantially reduced due to the reduction in the separation load. Most preferably, the solvent has a composition of approximately equal to or more than 50 percent by weight of the aldehydes and approximately equal to or less than 50 percent by weight of the high boilers.

In the preferred embodiment, the solvent is comprised substantially of an aldehyde, or optionally is comprised substantially of one or more of the products produced in the hydroformylation reaction. In the hydroformylation reaction, the product will be generally include normal and iso aldehydes along with some alcohols. An illustrative exemplary embodiment includes using an olefin starting material comprised of propylene and the hydroformylation reaction is carried out to produce primarily n-butyraldehyde, among other products and by-products. The amount of solvent employed is not critical to the present invention and need only be that amount sufficient to dissolve the catalyst into the hydroformylation reaction solution. Suitable amounts of solvent are in the range of about 5 percent by weight to 99 percent by weight based on the total weight of the starting materials of the hydroformylation reaction solution upon start up of the reaction.

According to the method of the present invention, the hydroformylation reactor may be optionally equipped such that the solvent is supplied in an initial charge upon the start of the hydroformylation reaction in an amount suitable to dissolve the catalyst and reactants. When the solvent is comprised at least partially, or optionally substantially of one or more of the aldehyde products of the hydroformylation reaction, an initial charge of the solvent is supplied, and then as the hydroformylation reaction progresses, a desired amount of the aldehyde product is removed from the reactor and recycled back to the reactor as the solvent. The amount of solvent supplied is not limited and generally need only be that minimum suitable amount necessary to promote dissolution of the catalyst, and optionally the reactants, into solution. By using aldehydes as the solvent, the solvent recovery units attendant in the prior art systems may be suitably adapted to the lesser recovery load such as by reducing their size, or such units may even be eliminated altogether.

Of significant advantage, the aldehydes exhibit a lower boiling temperature than conventional solvents. By employing aldehydes as the solvent, the temperature of the entire system is lowered. The system includes the hydroformylation reactor, the downstream catalyst process path, and the separation system. Thus by employing aldehydes and/or the hydroformylation reaction products as the solvent for the hydroformylation system, the operating temperature of the entire system is reduced as compared to systems employing conventional solvents. Conventional hydroformylation systems typically operate at temperatures of 100° C. and above and are subject to the formation of large amounts of high boilers in both the hydroformylation reaction and in the attendant separation systems and/or processes. Indeed the conventional separation systems and/or processes often reach quite high temperatures, such as temperatures of 130° C. and greater. By employing an aldehyde at least partially as the solvent, or optionally at least partially the aldehyde products, the present invention has the additional advantage of promoting a lower temperature process thereby reducing the formation of high boilers and minimizing the degradation of the catalyst and ligand throughout the entire system.

While the present invention provides for the substantial suppression of by-production of high boilers, they do form and accumulate over time. However, the formation of high boilers in the present invention is so slow that said components need be removed only periodically such as once a year or longer. This is in great contrast to the prior art methods where high boilers are frequently removed. Moreover, since the production rate of high boilers is very low in the method of the present invention, when the high boilers are purged, this can be accomplished by purging the small amount of high boilers with the aldehyde removal stream. Thus, due to the slow rate of high boiler build-up, a sufficient amount of high boilers can be easily removed in contrast to the prior art systems which often require specific high boiler separation units.

The particular reactants or starting materials for producing products from one or more reactions, as well as certain of the hydroformylation reaction conditions of the processes are not critical features of the present invention. The method of the present invention may correspond to and be employed with any of the heretofore known hydroformylation systems and their reactor and separation system topologies, although in the preferred embodiment many of the separation system units may be reduced or eliminated. With respect to the olefinic compound employed in the present invention as one of the starting materials of the hydroformylation reaction solution (also referred to as a reactant material), there is no critical limitation to its composition. Illustrative specific olefinic compounds include single olefin or a mixture of olefins. Representative olefinic compounds may be of high purity, or of low purity such as an olefin which also contains other hydrocarbons, such as paraffins and the like. Representative of a more preferred olefinic compound, olefin(s) having from 2 to 20 carbon atoms, or any mixtures thereof are suitably employed. More preferably, the olefinic compounds have from 2 to 8 carbon atoms, with propylene as the olefinic compound being most preferred. When using propylene as the olefin precursor, the hydroformylation reaction produces butyraldehyde, both the normal and iso forms, and optionally also produces butyl alcohol.

Regarding the catalyst, the catalyst useful in the method of the present invention includes a metal organophosphorus ligand complex catalyst. The catalyst is not limited, however it is preferred that the catalyst be selected such that it is active at the hydroformylation reaction temperature. For purposes of the description of the present invention, the term "active" as it is used to describe the catalyst herein is intended to convey that the catalyst exhibits catalytic activity in the hydroformylation reactor. The amount or quantity of catalytic activity exhibited for the catalyst to be considered active in this context is not limited. Any catalytic activity, whether or not it is economically desirable, shall render the catalyst as active. Notwithstanding the above, while there is no limitation to the activity of the catalyst, for economic conditions it is preferred, however, that the catalyst be selected such that it exhibits a reaction half time of approximately one hour or less at the selected hydroformylation reaction temperature and pressure. A catalyst which exhibits a reaction half time greater than one hour may also be used, however the reactor volume and the residence time will increase.

Representative catalysts suitable in the method of the present invention include catalysts comprised of metal compounds selected from Groups VIII to X of the Periodic Table, and having an organophosphorus compound as a ligand. Illustrated specific catalysts employable in the method of the present invention include organophosphorus compounds selected from the group consisting of trialkylphosphines, triarylphosphines, triarylphosphine having hydrogen substituted by a sulfonic group or halogen, tricycloalkylphosphines, alkyldiarylphosphines, dialkylarylphosphines, cycloalkyldiarylphosphines, dicycloalkylarylphosphines, alkylcyclodialkylphosphines, dialkylcycloalkylphosphines, trialkly phosphites, triarly phosphites, or bisphosphines and bisphosphites. Representative preferred embodiments of the catalyst employable in the present invention include bisphosphine and bisphosphite ligand compounds. More specifically the catalyst is described in further detail below.

Examples of phosphite compounds which may be used in the method of the present invention include, but are not particularly limited to, triaryl phosphites, trialkyl phosphites, arylalkyl phosphites, or any other phosphite. Bisphosphite and polyphosphite compounds or the like which have combinations of these in the same molecule are also included.

More specifically, monophosphite compounds can be divided into the two following compound groups. That is, one group of compounds comprises phosphite compounds having a cyclic structure, with phosphorus atoms contained in the cyclic structure. The other group of compounds comprises phosphite compounds that have no cyclic structure containing phosphorus atoms.

Among monophosphite compounds which can be used in the hydroformylation reaction encompassed in the present invention, those phosphite compounds represented by the following formula are preferred among the latter compounds, that is, phosphite compounds that have no cyclic structure containing phosphorus atoms.

$$P(OR1)(OR2)(OR3) \quad (1)$$

Where R1, R2, and R3 are optionally $C_1$ to $C_{30}$ substituent-bearing alkyl groups, cycloalkyl groups, aryl groups, aralkyl groups, and heteroaryl groups. Examples of substituents are not particularly limited, provided that they do not inhibit the reaction, and include $C_1$ to $C_{20}$ alkyl groups, cycloalkyl groups, alkoxy groups, halogens, alkylamino groups, acyl groups, acyloxy groups and alkoxycarbonyl groups.

Desirable compounds among these are organic phosphite compounds in which at least one of R1, R2, or R3 in General Formula 1 is independently a substituted aryl group represented by General Formula 2:

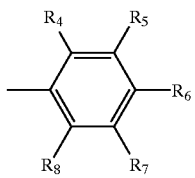

(2)

where R4 is —C(R9)(R10) R11 or an optionally substituted aryl group (R9, R10, and R11 are each independently a hydrogen atom, fluorohydrocarbon group or hydrocarbon group); R4 preferably has steric hindrance as a whole equal to or greater than isopropyl groups; and R5, R6, R7, and R8 are each independently a hydrogen atom or organic group, and may also be condensed aromatic rings or hetero rings with adjacent substituents such as R6 and R7 bonded to each other.

Specific examples of such compounds include diphenyl (2,4-di-tert-butylphenyl) phosphite, diphenyl(2-isopropylphenyl)phosphite, bis(2-tert-butyl-4-methylphenyl)phenylphosphite, diphenyl (3,6-ditert-butyl-2-naphthyl) phosphite, bis(2-naphthyl)(3,6-di-tert-butyl-2-naphthyl) phosphite, bis(3,6,8-tri-tert-butyl-2-naphthyl) phenylphosphite, and bis(3,6,8-tri-tert-butyl-2-naphthyl)(2-naphtyl)phosphite.

Preferred compounds among these include organic phosphite compounds in which all of R1, R2, and R3 in General Formula 1 are substituted aryls represented by the aforementioned General Formula 2.

Specific examples of such compounds include tris(2,4-di-tert-butylphenyl) phosphite, tris(2-tert-butyl-4-methylphenyl)phosphite, tris(2-tert-butyl-4-methoxyphenyl) phosphite, tris(o-phenylphenyl)phosphite, tris(o-methylphenyl)phosphite, bis(3,6-di-tert-butyl-2-naphthyl)(2,4-di-tert-butylphenyl)phosphite, bis(3,6-di-tert-butyl-2-naphthyl)(2-tert-butylphenyl)phosphite, tris (3,6-di-tert-butyl-2-naphthyl)phosphite, and tris(3,6-di-tert-amyl-2-naphtyl)phosphite.

Other monophosphite compounds which can be used in the reaction encompassed in the present invention include phosphite compounds represented by the following formula, which are phosphite compounds of the other group of compounds that have a cyclic structure, with phosphorus atoms contained in the cyclic structure of General Formula 3:

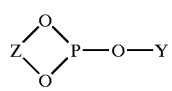

(3)

Where Z is a divalent organic group, and Y is an optionally substituted monovalent organic group.

Typical divalent groups represented by Z in General Formula 3 include those where Z is a divalent alkyl group ordivalent aromatic group. Examples of divalent alkyl groups include alkylene, alkyleneoxyalkylene, and alkylene-NR12-alkylene (where R12 is hydrogen or a monovalent hydrocarbon group), alkylene-S-alkylene, cycloalkylene, and similar groups. Examples of divalent aromatic groups include arylene, biarylene, arylenealkylene, arylenealkylenearylene, aryleneoxyarylene, aryleneoxyalkylene, arylene-NR12-arylene and arylene-NR12-alkylene (where R12 is hydrogen or a monovalent hydrocarbon group), arylene-S-alkylene, and arylene-S-arylene.

Examples of desirable phosphite compounds represented by General Formula 3 include phosphite compounds represented by the following General Formula 4:

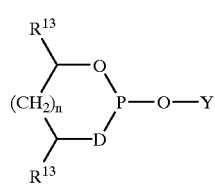

(4)

where R13 are each independently a hydrogen, optionally substituted alkyl group, cycloalkyl group, or optionally substituent-bearing aryl group; n is an integer of 0 to 4; and Y is an optionally substituted monovalent organic group.

R13 in Formula 4 is typically a methyl group, ethyl group, phenyl group, tolyl group, benzyl group, naphthyl group, hydroxymethyl group, hydroxyethyl group, trifluoromethyl group, or the like.

Y in General Formula 4 is preferably an aryl group, such as that represented by General Formula 2, having a substituent at the adjacent carbon atom of the carbon atoms bonded to the oxygen atom.

Other examples of desirable phosphite compounds include those of the following General Formula 5:

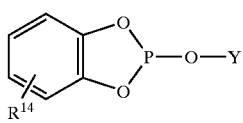
(5)

where R14 is any substituent at the o, m or p position, or form a condensed aromatic ring, such as a naphthyl ring with the original adjacent phenyl ring; and Y is an optionally substituted monovalent organic group.

R14 in Formula 5 is typically an alkyl group, cycloalkyl group, alkoxy group, acyl group, acyloxy group, or optionally substituent-bearing aryl group. Naphthyl and the like are examples of the condensed aromatic rings.

Y in General Formula 5 is preferably an aryl group, such as that represented by General Formula 2, having a substituent at the adjacent carbon atom of the carbon atoms bonded to the oxygen atom.

Other examples of desirable phosphite compounds include those represented by General Formula 6:

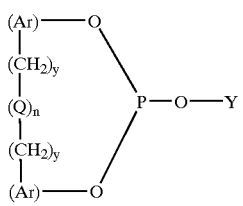
(6)

This is a diorganophosphite compound, where Ar are each independently an optionally substituted aryl group; y are each independently 0 or 1; Q is a divalent bridge group selected from the group comprising of —CR15R16—, —O—, —S—, —NR17—, —SiR18R19—, and —CO— (where R15 and R16 are each independently selected from the group comprising of hydrogen, $C_1$ to $C_{12}$ alkyl groups, phenyl, tolyl, and anisyl; and R17, R18, and R19 are each independently a hydrogen or methyl group); n is 0 or 1; and Y is an optionally substituted monovalent organic group.

Y in General Formula 6 preferably includes optionally substituted monovalent hydrocarbons selected from the group consisting of $C_1$ to $C_{20}$ alkyl groups (primary, secondary, and tertiary alkyl groups such as methyl, ethyl, n-propyl, isopropyl, butyl, sec-butyl, t-butyl, t-butylethyl, t-butylpropyl, n-hexyl, amyl, sec-amyl, t-amyl, iso-octyl, 2-ethylhexyl, decyl, octadecyl), as well as aryl groups such as optionally substituent-group bearing aryl groups, including α-naphthyl and β-naphthyl. Examples of substituents for aryl groups include $C_1$ to $C_{20}$ alkyl groups, cycloalkyl groups, alkoxy groups, halogens, alkylamino groups, acyl groups, acyloxy groups, and alkoxycarbonyl groups.

Examples of more desirable phosphite compounds represented by General Formula 6 include those represented by General Formula 7 or 8:

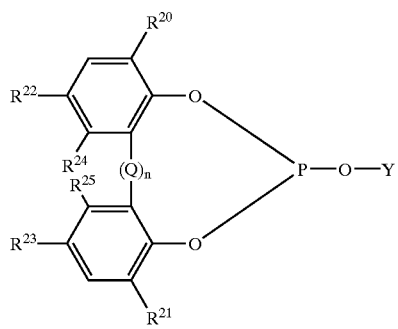
(7)

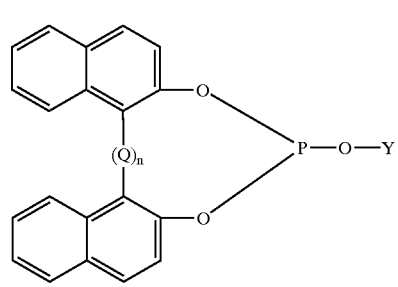
(8)

Q, Y and n are defined in the same manner as in Formula 6 above. R20, R21, R22, R23, R24, and R25 are $C_1$ to $C_{20}$ alkyl groups, cycloalkyl groups, alkoxy groups, halogen, alkylamino groups, acyl groups, acyloxy groups, and alkoxycarbonyl groups.

Specific examples of such compounds include those represented by the following formulas:

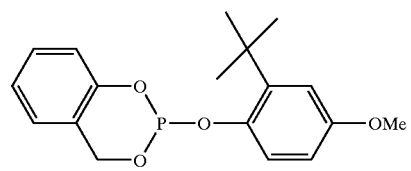

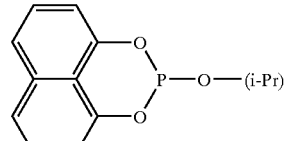

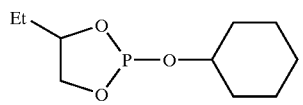

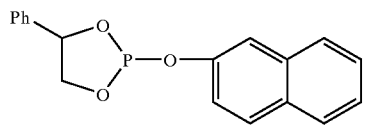

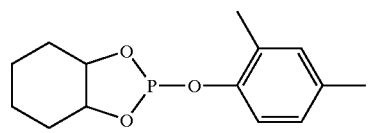

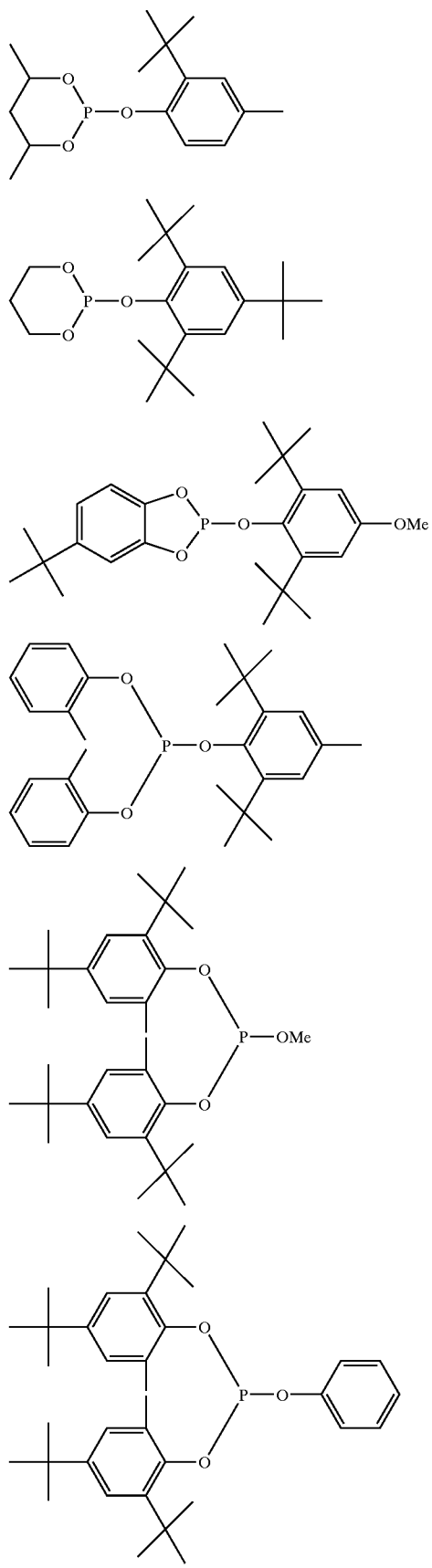

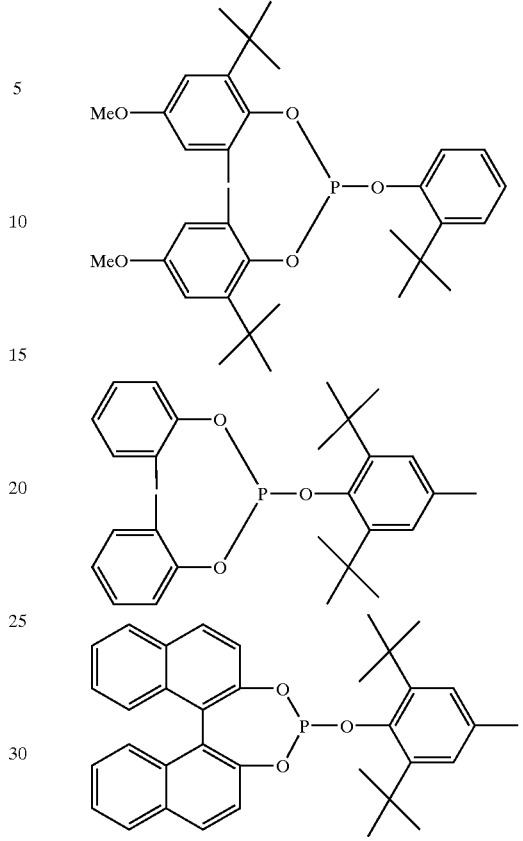

Examples of bisphosphite and polyphosphite ligands which can be used in the reaction encompassed in the present invention include compounds represented by General Formula 9.

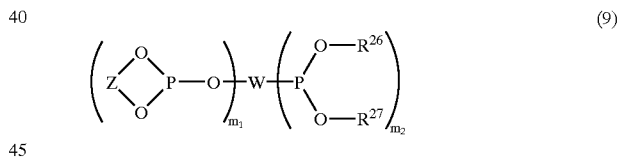

(9)

Where Z represents the same divalent organic groups as those defined in General Formula 3 above; and R26 and R27 are each independently optionally $C_1$ to $C_{30}$ substituent-bearing alkyl groups, cycloalkyl groups, aryl groups, aralkyl groups, and heteroaryl groups. Examples of substituents are not particularly limited, provided that they do not inhibit the reaction, and include $C_1$ to $C_{20}$ alkyl groups, cycloalkyl groups, alkoxy groups, halogens, alkylamino groups, acyl groups, acyloxy groups, and arkoxycarbonyl groups. Examples of end organic groups represented by R26 and R27 include $C_1$ to $C_{20}$ straight-chain or branched alkyl groups such as methyl, ethyl, n-propyl, isopropyl, n-butyl, s-butyl, t-butyl, n-pentyl, isopentyl, neopentyl, t-pentyl, and t-hexyl; $C_3$ to $C_{20}$ cycloalkyl groups such as cyclopropyl, cyclohexyl, cyclooctyl, and adamantyl; optionally substituent-bearing aryl groups such as phenyl, α-naphthyl, β-naphthyl, methoxyphenyl, dimethoxyphenyl, methoxycarbonylphenyl, cyanophenyl, nitrophenyl, chlorophenyl, dichlorophenyl, pentafluorophenyl, methylphenyl, ethylphenyl, dimethylphenyl, trifluoromethylphenyl, methylnaphthyl, methoxynaphthyl, chloronaphthyl, nitronaphthyl, and tetrahydronaphthyl;

aralkyl groups such as benzyl; and heterocyclic aromatic groups such as pyridyl, methylpyridyl, nitropyridyl, pyrazyl, pyrimidyl, benzofuryl, quinolyl, isoquinolyl, benzimidazolyl, and indolyl. W is an optionally substituted m-valent hydrocarbon group, m1 and m2 are each independently an integer of 0 to 6, where m=m1+m2 has a value of 2 to 6. When m1 and m2 are each more then 2, then Z, R26, and R27 may be the same as or different from each other.

Examples of more desirable phosphite compounds include compounds in which the Z in General Formula 9 is Z as defined in Formulas 4, 5, and 6, as well as phosphite compounds in which Z is represented by a combination of the aforementioned formulas. R26 and R27 preferably are each independently an optionally substituent-bearing aryl group. Specific examples include phenyl, 2-methylphenyl, 3-methylphenyl, 4-methylphenyl, 2,4-di-methylphenyl, 2,5-di-methylphenyl, 2,6-di-methylphenyl, 2-methoxyphenyl, 3-methoxyphenyl, 4-methoxyphenyl, 2,4-dimethoxyphenyl, 2,5-dimethoxyphenyl, 2,6-dimethoxyphenyl, α-naphthyl, 3-methyl-α-naphthyl, 3,6-dimethyl-α-naphthyl, β-naphthyl, 1-methyl-β-naphthyl, and 3-methyl-β-naphthyl.

These are compounds in which W is an optionally substituted m-valent hydrocarbon group, which is an alkylene, arylene, or is represented by arylene-$(CH_2)y$-$(Q)n$-$(CH_2)y$-arylene (where the arylenes are each independently an optionally substituted arylene; Q are each independently a bridge group selected from the group consisting of —CR28R29—, —O—, —S—, —NR30—, —SiR31R32—, and —CO— (where R28 and R29 are each independently selected from the group comprising of hydrogen and alkyls; and R30, R31, and R32 are each independently —H or —$CH_3$); and y and n are each independently 0 or 1).

Specific examples of divalent organic groups represented by W include 1,2-ethylene, 1,3-propylene, 1,3-dimethyl-1,3-propylene, 1,4-butylene, 1,5-pentylene, 1,6-hexylene, 1,8-octylene, 1,2-phenylene, 1,3-phenylene, 2,3-naphthylene, 1,8-naphthylene, 1,1'-biphenyl-2,2'-diyl, 1,1'-binapthyl-7,7'-diyl, 1,1'-binaphthyl-2,2'-diyl, 2,2'-binaphthyl-1,1'-diyl, and 2,2'-binaphthyl-3,3'-diyl groups.

Even more desirable compounds include those in which Z in General Formula 9 is Z defined in General Formula 6 above, and compounds in which W is represented by General Formula 10.

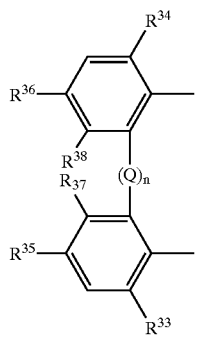

(10)

R37 and R38 are each independently a $C_1$ to $C_{12}$ alkyl group, cycloalkyl group, alkoxy group, silyl group, siloxy group, or a halogen atom or hydrogen atom. Examples include hydrogen atoms, or methyl, ethyl, n-propyl, isopropyl, n-butyl, methoxy, ethoxy, and n-propoxy groups, and fluorine, chlorine, bromine, or iodine atoms. R33 through R36 are each independently a $C_1$ to $C_{20}$ alkyl, cycloalkyl, alkoxy, silyl, or siloxy group, or a halogen or hydrogen atom. Examples include hydrogen, methyl, ethyl, n-propyl, isopropyl, n-butyl, t-butyl, t-pentyl, neopentyl, t-hexyl, nonyl, decyl, methoxy, ethoxy, and t-butoxy groups. Specific examples of Formula 10 include those in which R35 and R37 and/or R36 and R38 each independently bond to each other to form part of a cyclic structure consisting of 3 to 40 carbons. A specific example is 1,1'-binaphthyl-2,2'-diyl.

More preferably, R26 and R27 in General Formula 9 are each independently an optionally substituted aryl, and W is a 1,1'-biphenyl-2,2'-diyl skeleton or substituted arylene-arylene having a 1,1'-biphenyl-2,2'-diyl skeleton, wherein R33 and R34 in General Formula 10 are each independently a $C_3$ to $C_{20}$ branched alkyl, and R35 and R36 are each independently a $C_1$ to $C_{20}$ branched alkyl or alkoxy. Specific examples thus include 3,3'-di-t-butyl-1,1'-binaphthyl-2,2'-diyl, 3,3'-6,6'-tetra-t-butyl-1,1'-binaphthyl-2,2'-diyl, 3,3'-di-t-butyl-6,6'-di-t-butoxy-1,1'-binaphthyl-2,2'-diyl, pentyl-1,1'-binaphthyl-2,2'-diyl, 3,3'6,6'-tetra-t-pentyl-1,1'-binaphthyl-2,2'-diyl, 3,3'-di-t-butyl-5,5'-dimethyl-1,1'-biphenyl-2,2'-diyl, 3,3',5,5'-tetra-t-butyl-1,1'-biphenyl-2,2'-diyl, 3,3',5,5'-tetra-t-pentyl-1,1'-biphenyl-2,2'-diyl, 3,3'-di-t-butyl-5,5'-dimethoxy-1,1'-biphenyl-2,2'-diyl, 3,3'-di-t-butyl-5,5',6,6'-tetramethyl-1,1'-biphenyl-2,2'-diyl, 3,3',5,5'-tetra-t-butyl-6,6'-dimethyl-1,1'-biphenyl-2,2'-diyl, 3,3',5,5'-tetra-t-pentyl-6,6'-dimethyl-1,1'-biphenyl-2,2'-diyl, 3,3'-di-t-butyl-5,5'-dimethoxy-6,6'-dimethyl-1,1'-biphenyl-2,2'-diyl, and 3,3',5,5'-tetra-t-butyl-6,6'-dichloro-1,1'-biphenyl-2,2'-diyl.

In the most desirable examples, W is limited to the above, and R37 and R38 are each independently a $C_1$ to $C_3$ alkyl, alkoxy, or halogen. Examples of substituents thereof include methyl, ethyl, n-propyl, isopropyl, methoxy, ethoxy, n-propoxy, and isopropoxy groups, and fluorine, chlorine, bromine, and iodine atoms. Examples of the most desirable bridge divalent organic groups thus include 3,3'-di-t-butyl-5,5',6,6'-tetramethyl-1,1'-biphenyl-2,2'-diyl, 3,3',5,5'-tetra-t-butyl-6,6'-dimethyl-1,1'-biphenyl-2,2'-diyl, 3,3',5,5'-tetra-t-butyl-6,6'-diethyl-1,1'-biphenyl-2,2'-diyl, 3,3',5,5'-tetra-t-butyl-6,6'-dimethoxy-1,1'-biphenyl-2,2'-diyl, 3,3'-di-t-butyl-5,5'-dimethoxy-6,6'-dichloro-1,1'-biphenyl-2,2'-diyl, and 3,3',5,5'-tetra-t-butyl-6,6'-difluoro-1,1'-biphenyl-2,2'-diyl.

Among the phosphite compounds which can be used in the reaction encompassed in the present invention, the following compounds set forth below are specific examples of the more desirable ones.

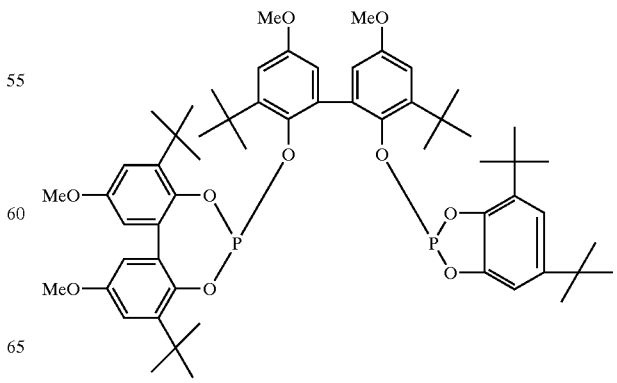

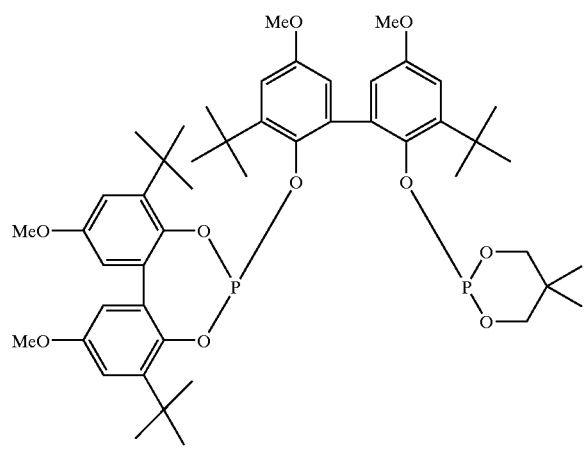
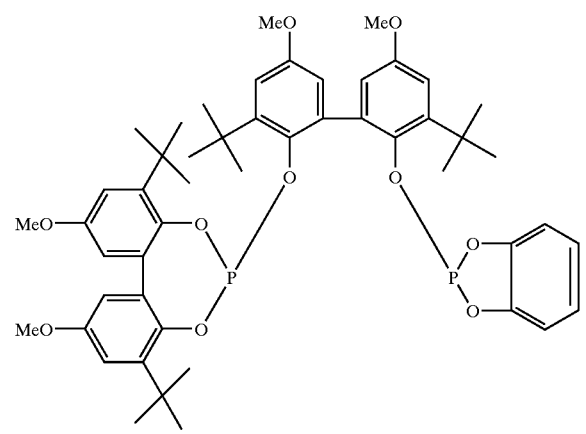
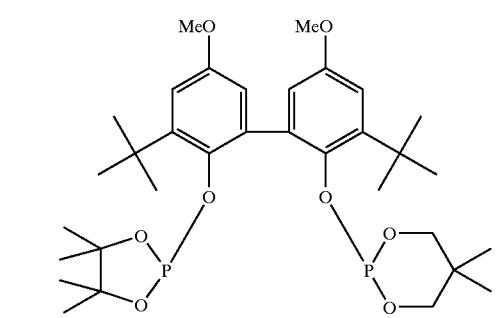
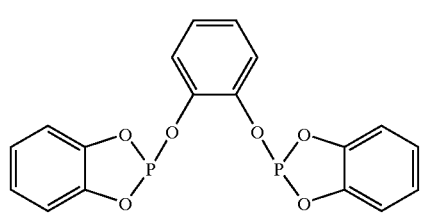
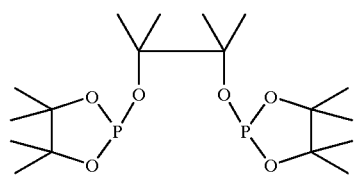
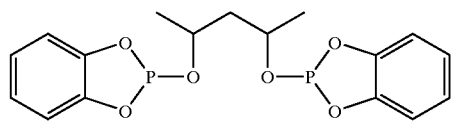
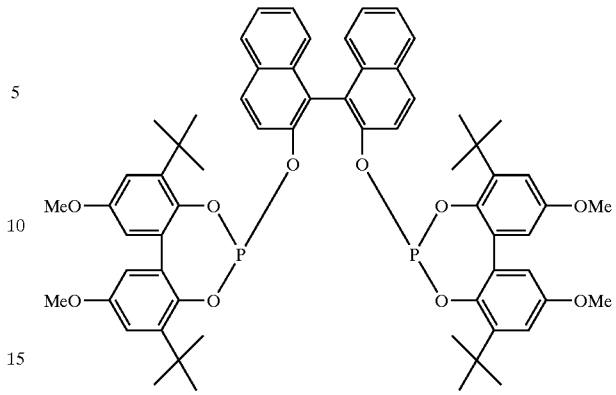
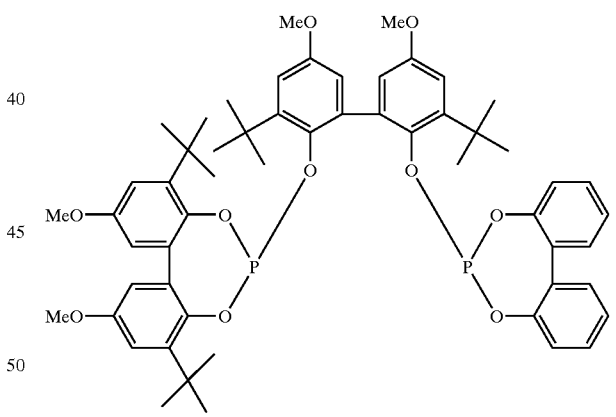
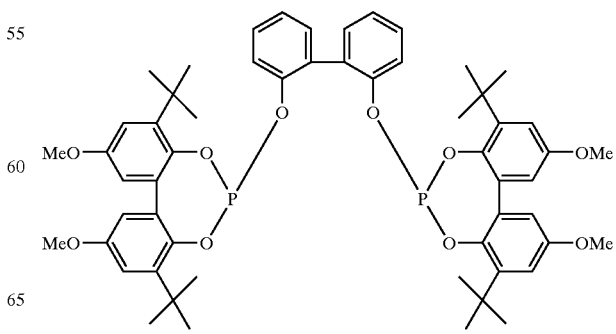

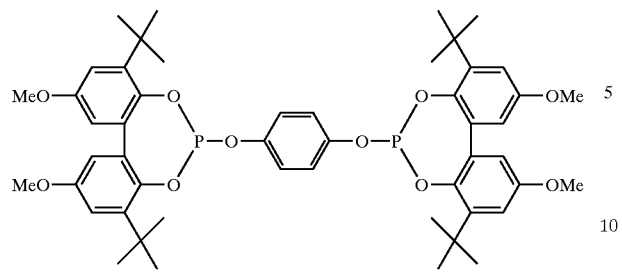
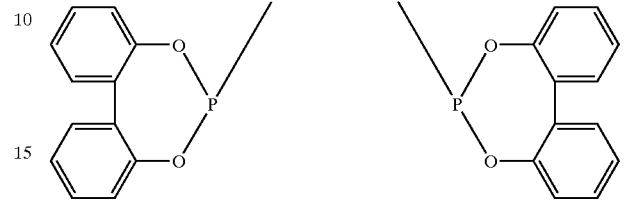
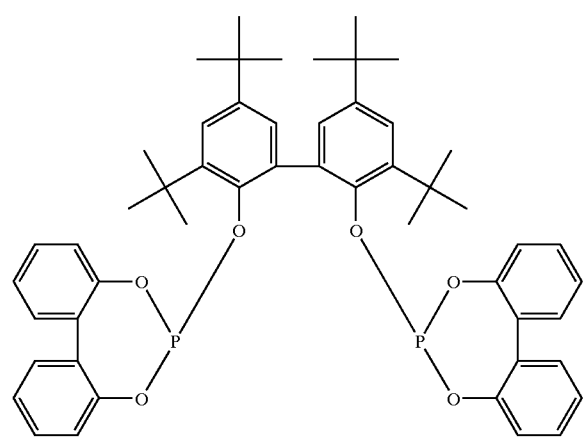
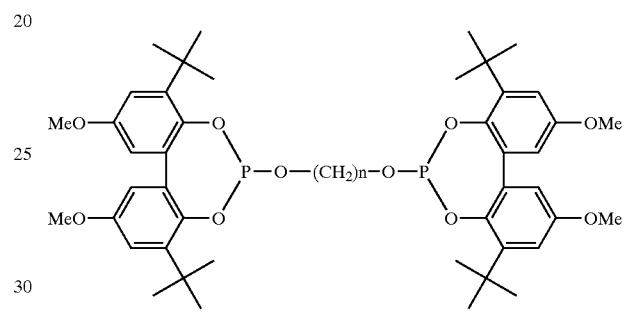
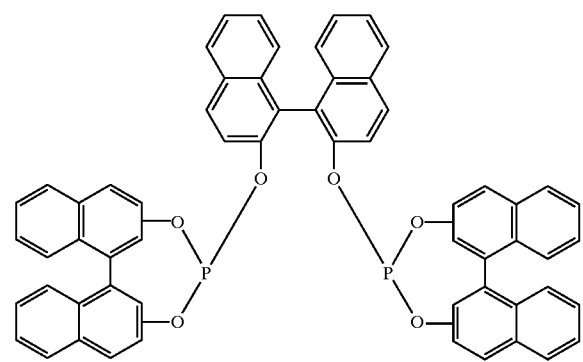
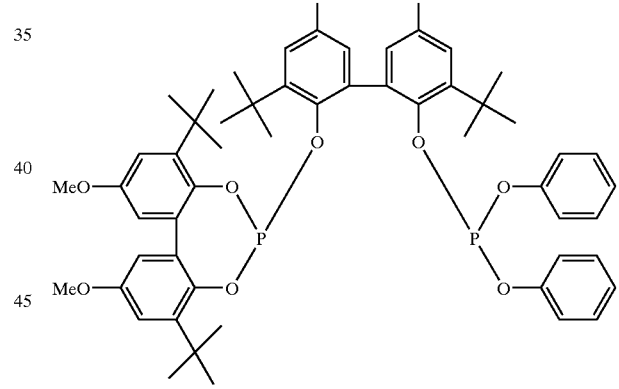
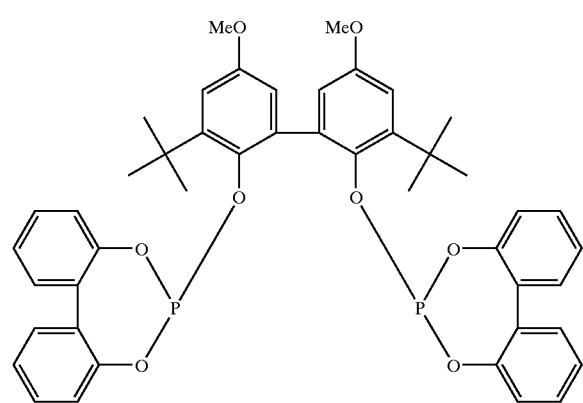
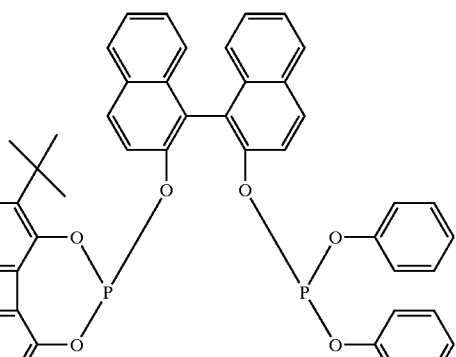

-continued
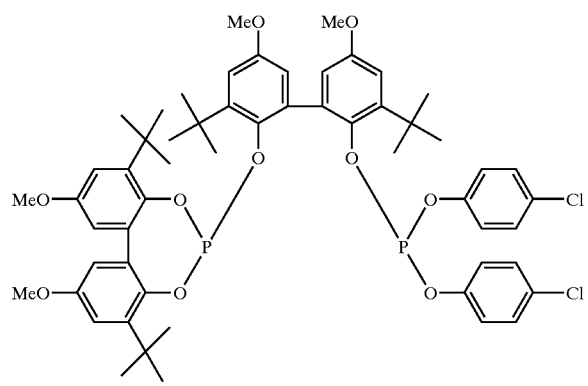
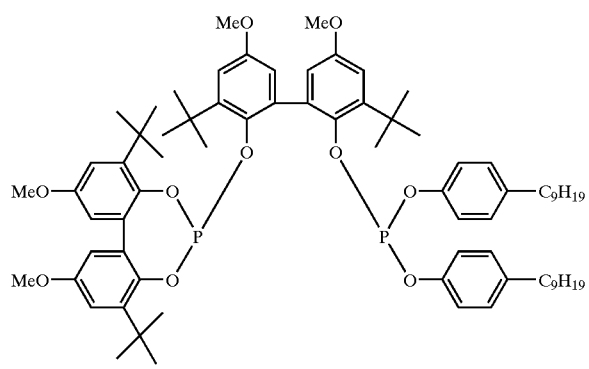
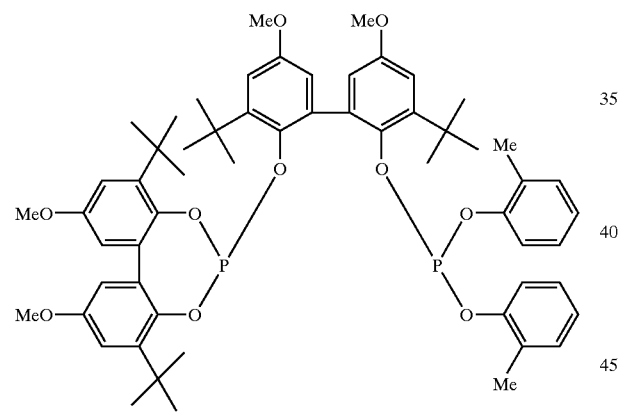
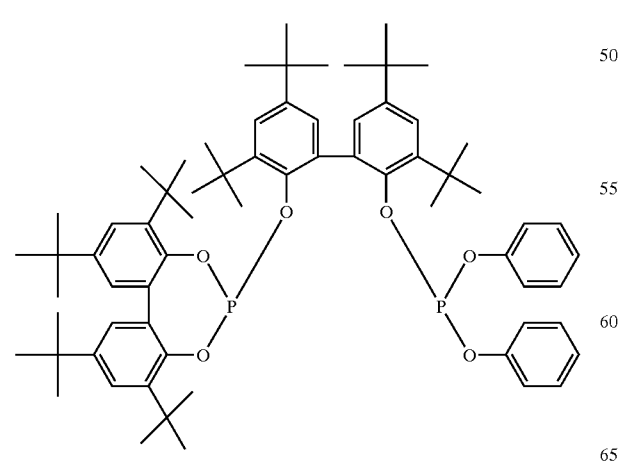
-continued
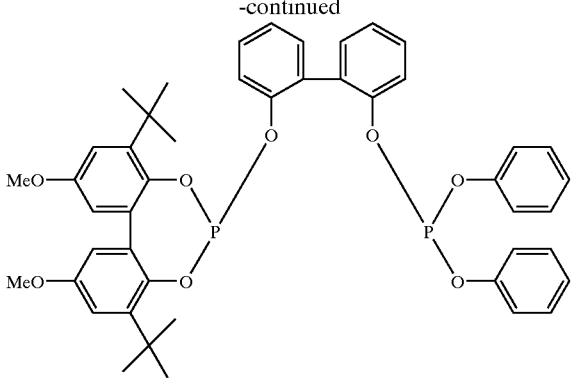
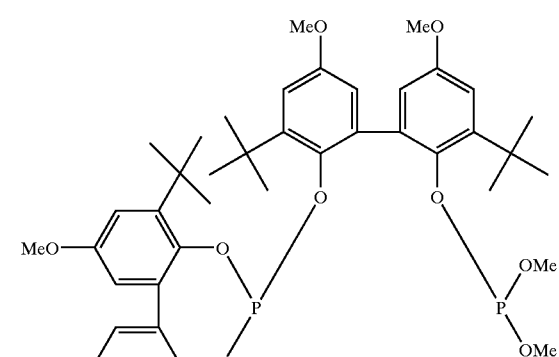
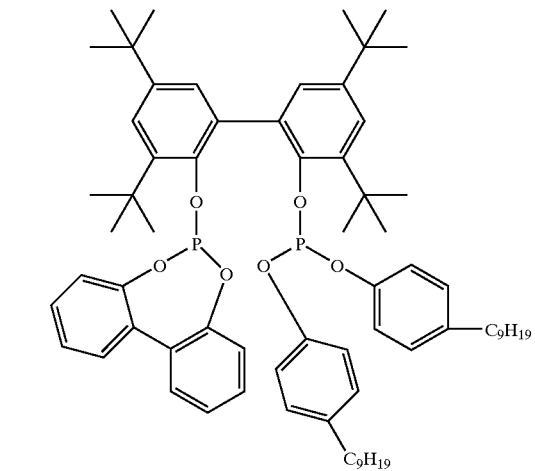
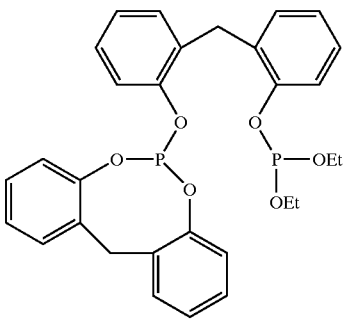

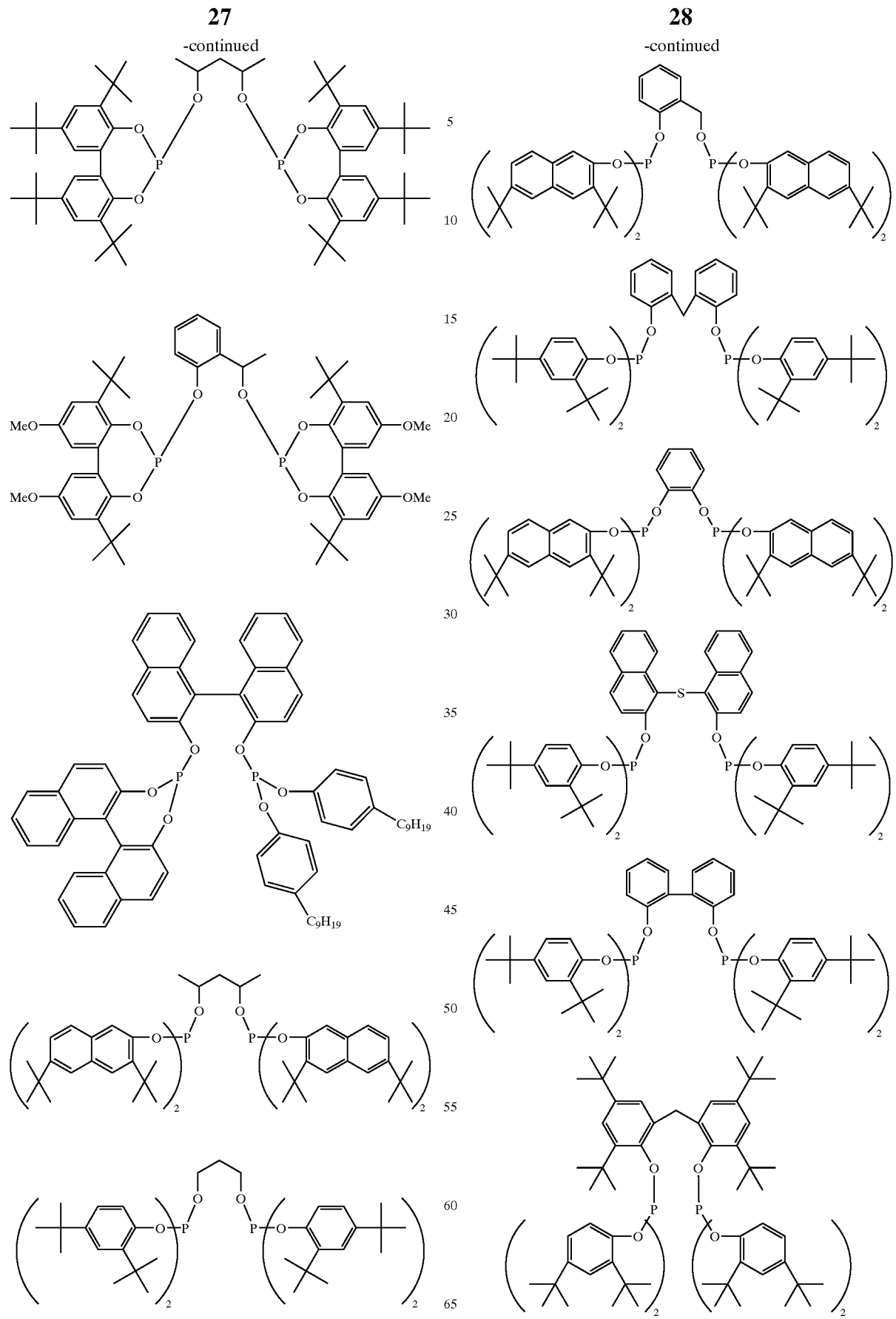

-continued
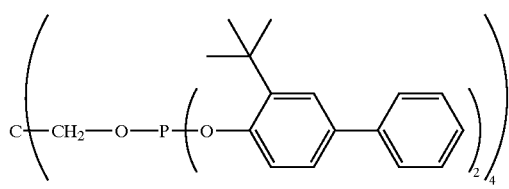
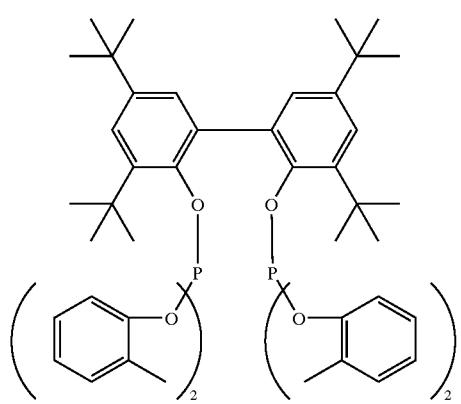
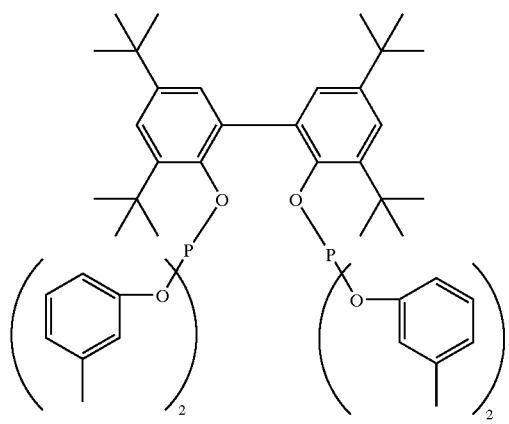
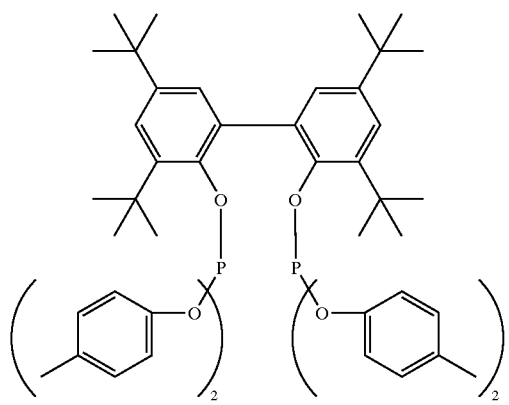
-continued
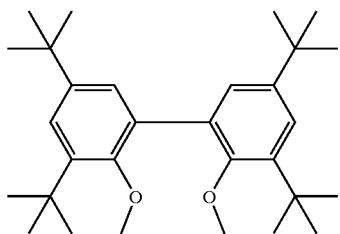
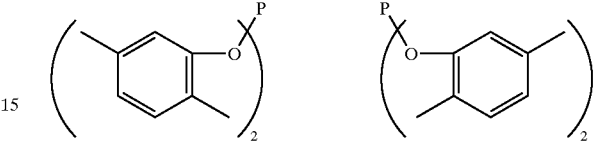
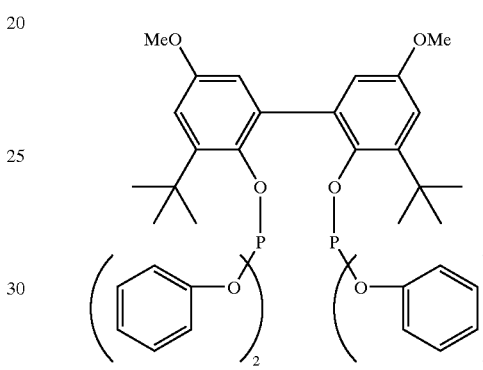
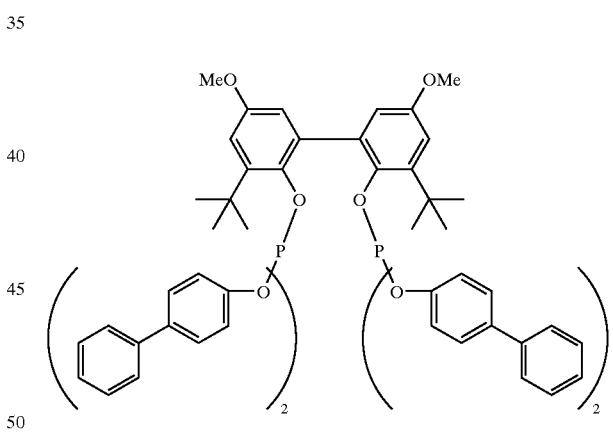
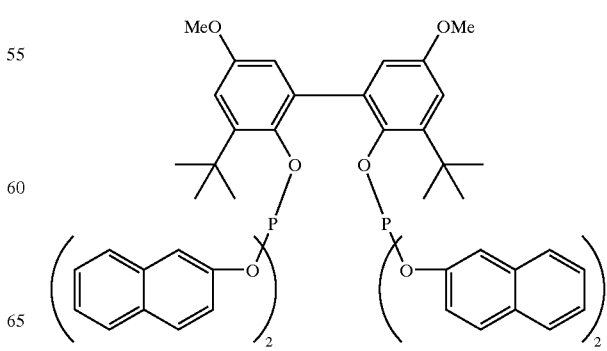

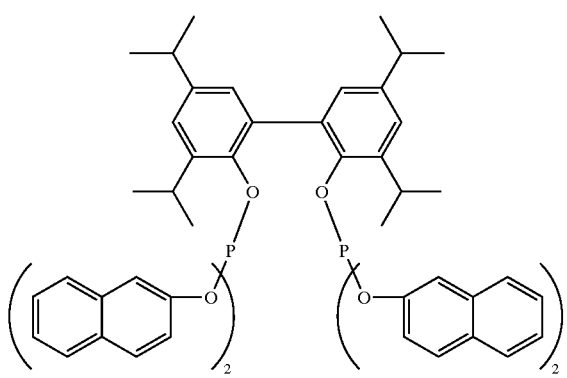
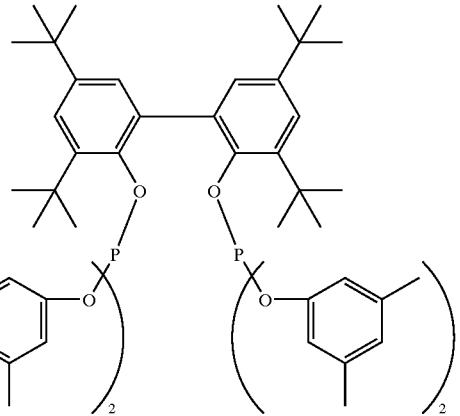
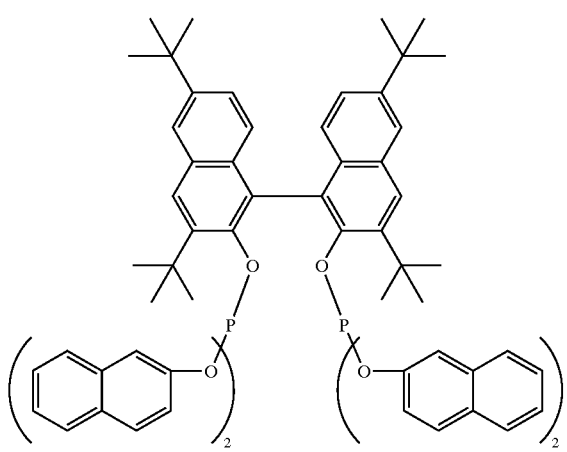
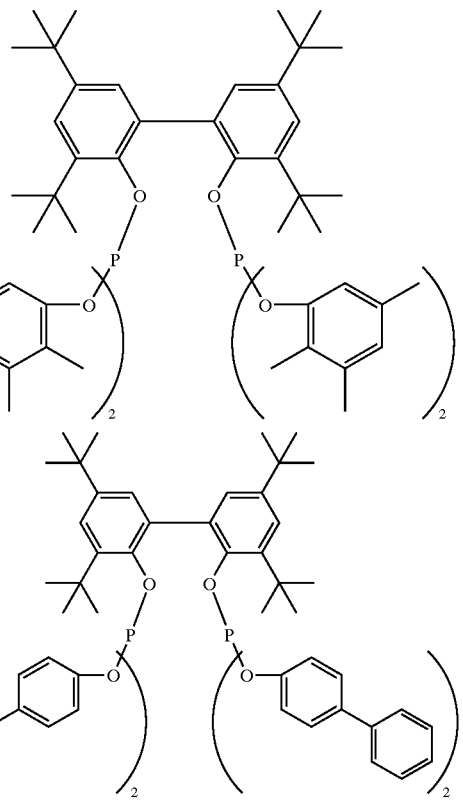
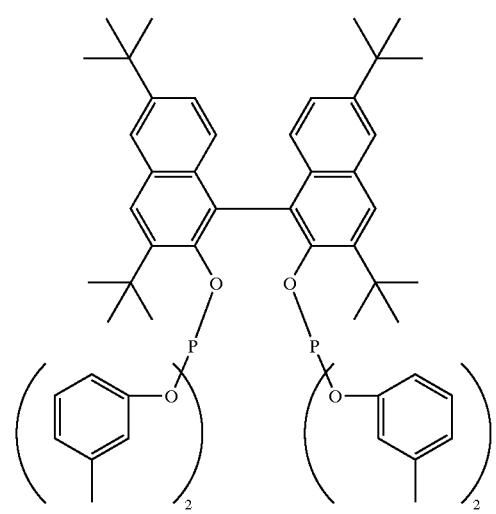

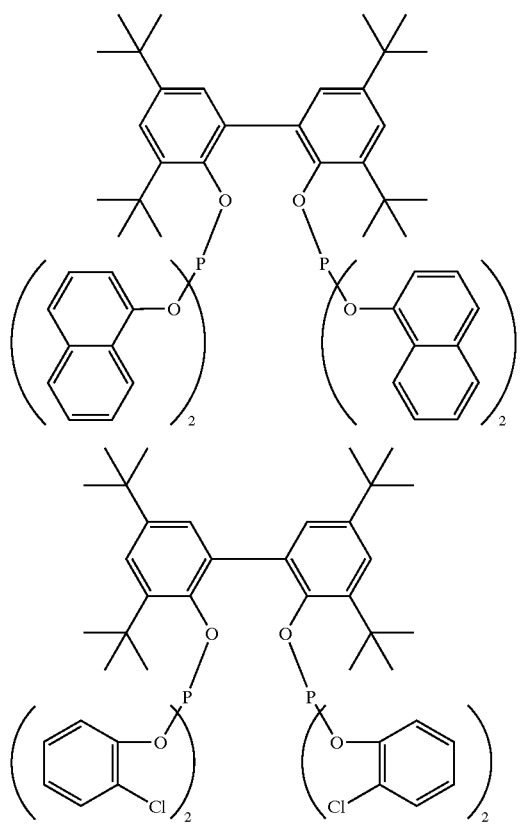
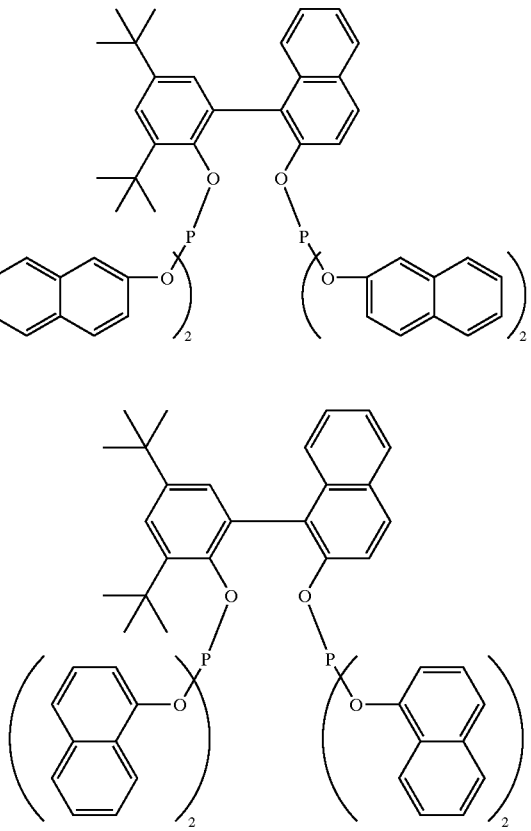
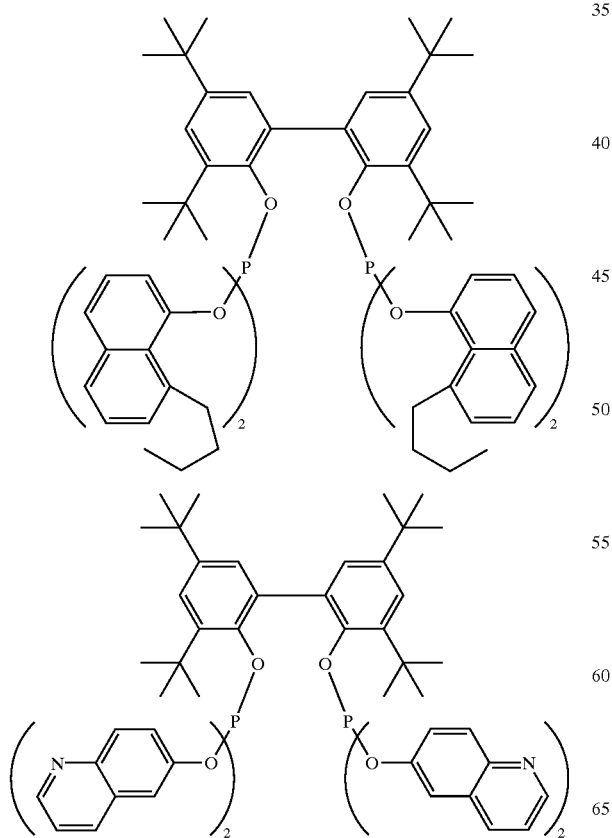
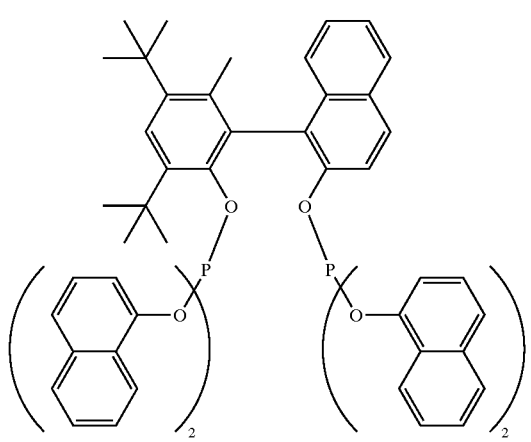

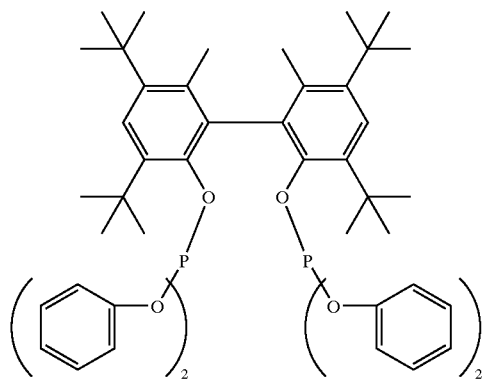
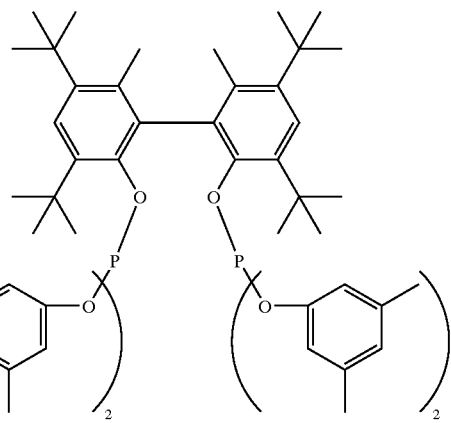
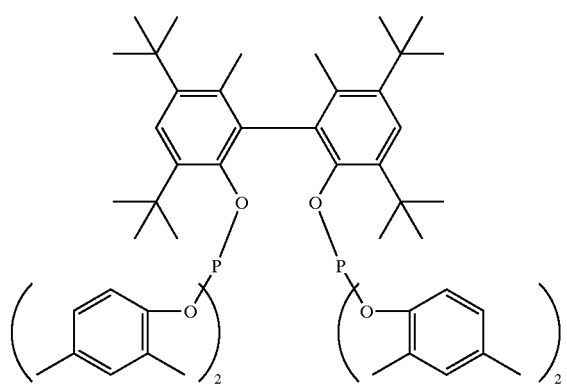
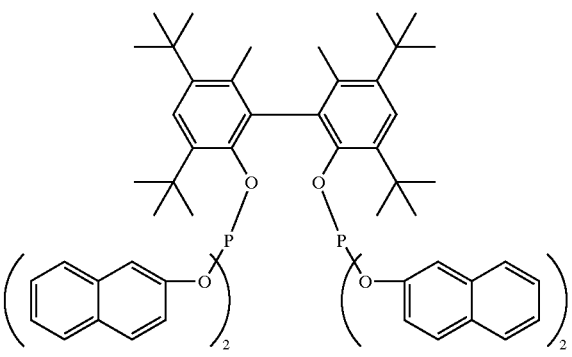
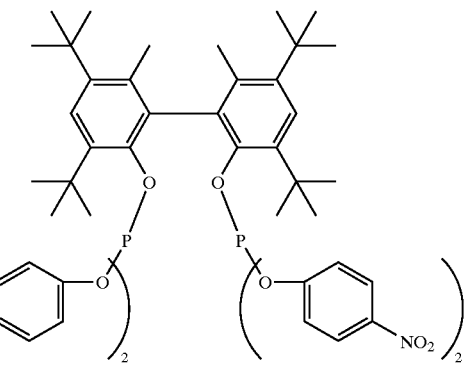
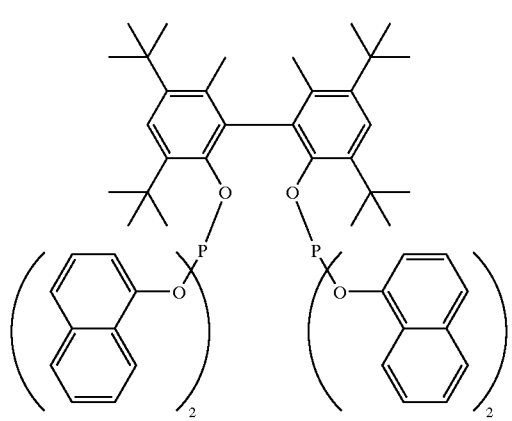
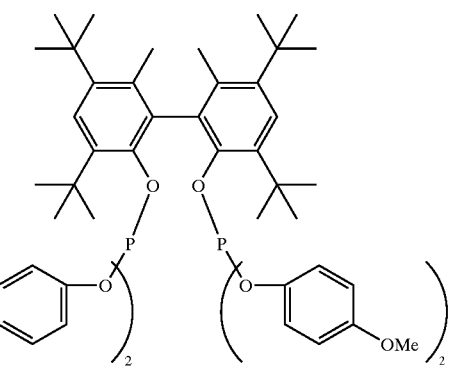

37
-continued
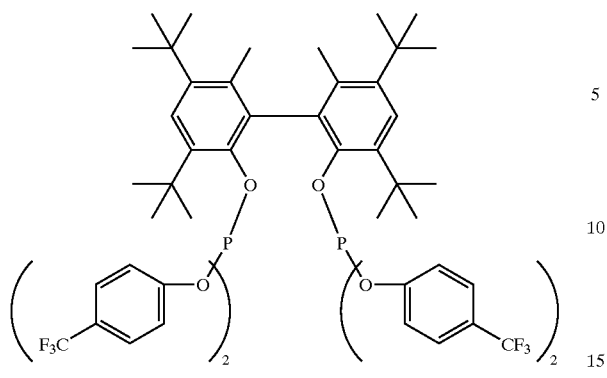
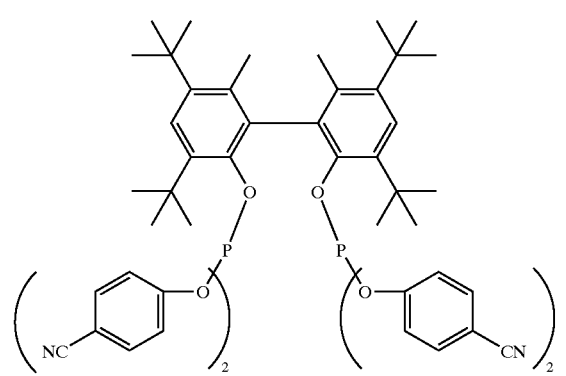
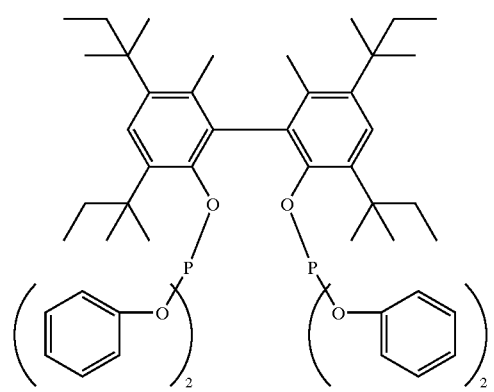
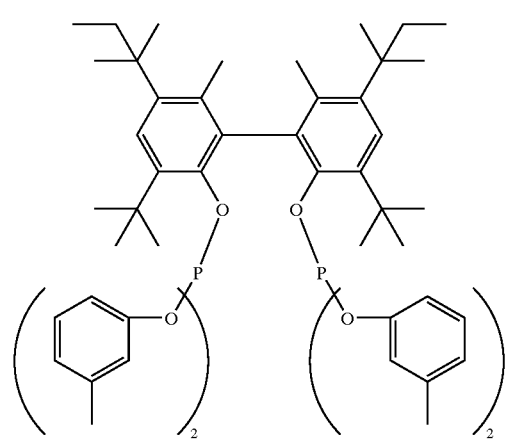
38
-continued
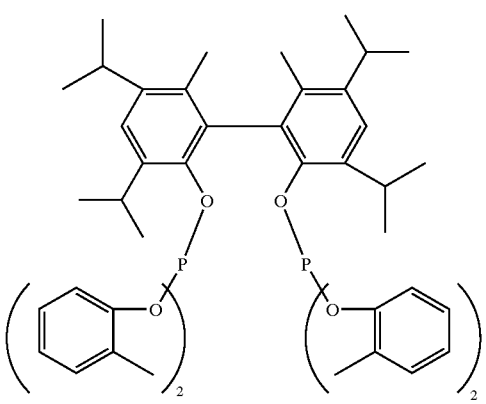
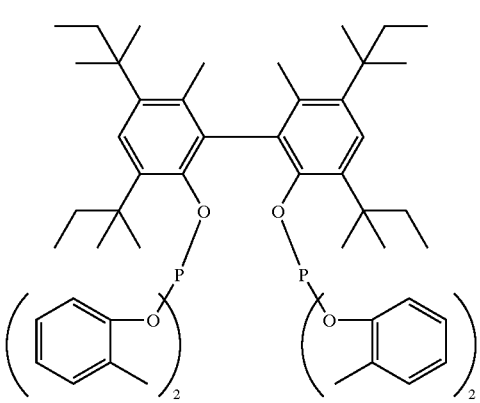
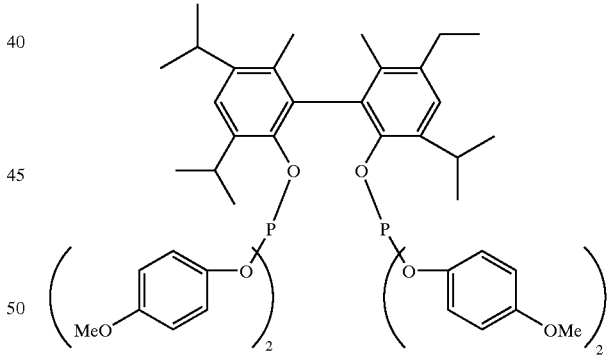
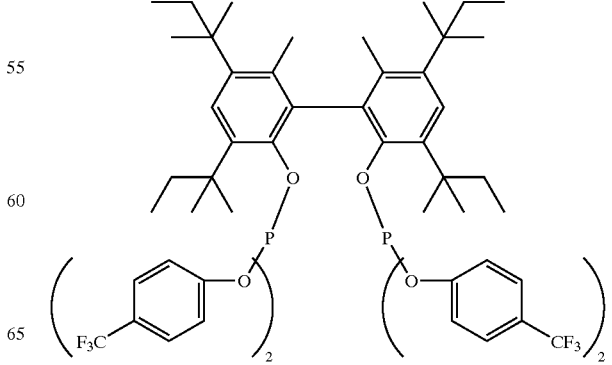

-continued
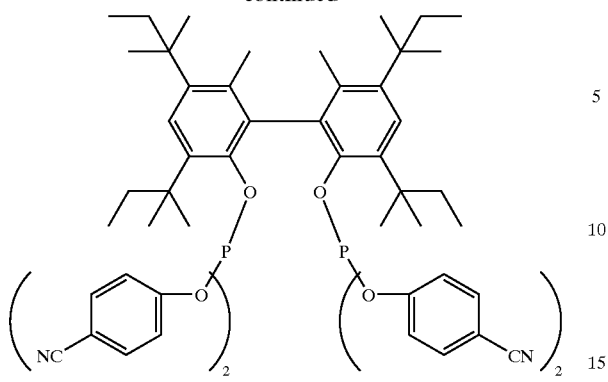
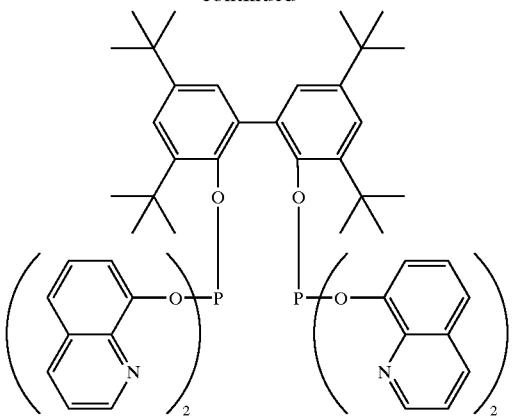
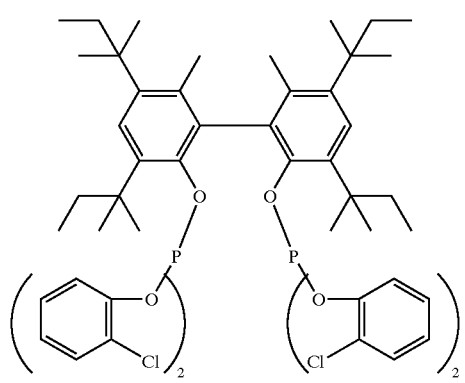
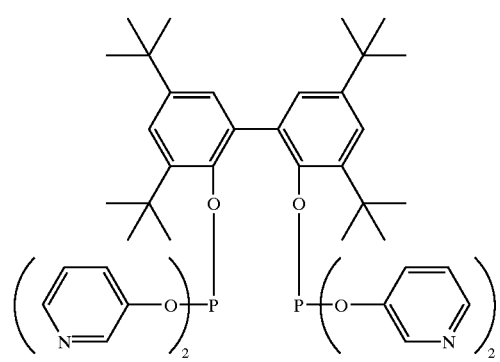
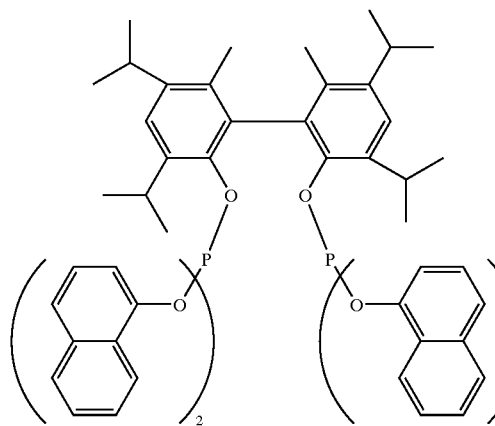
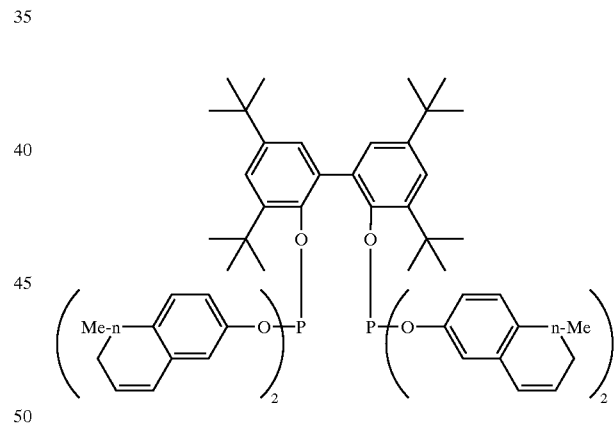
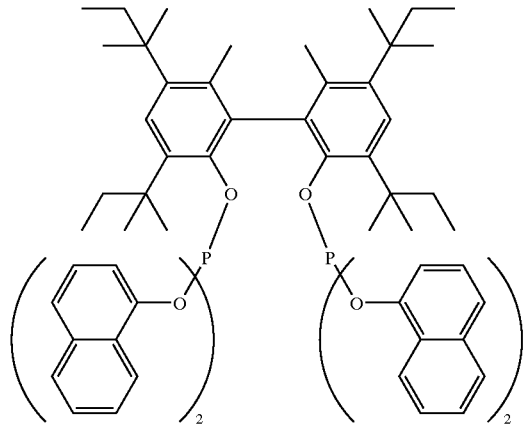
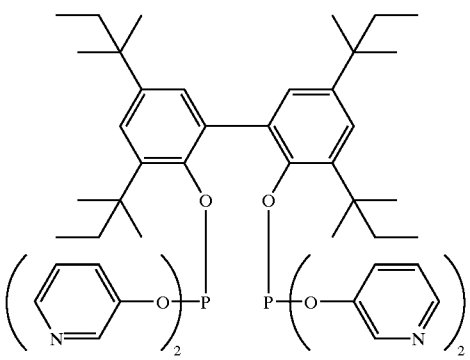

-continued
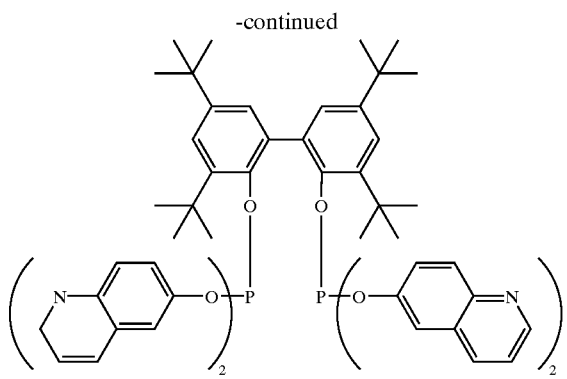
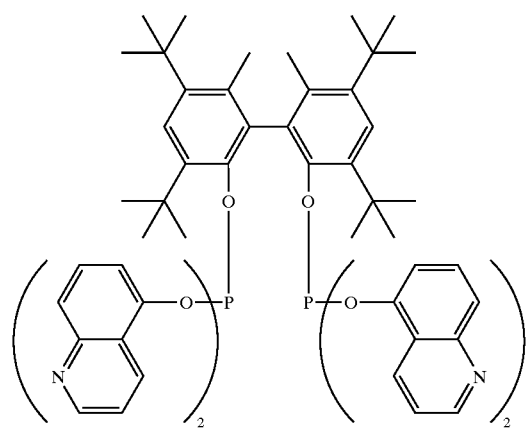
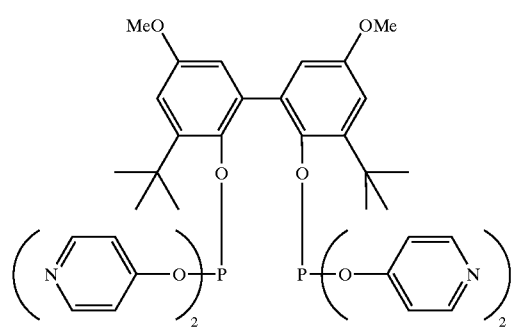
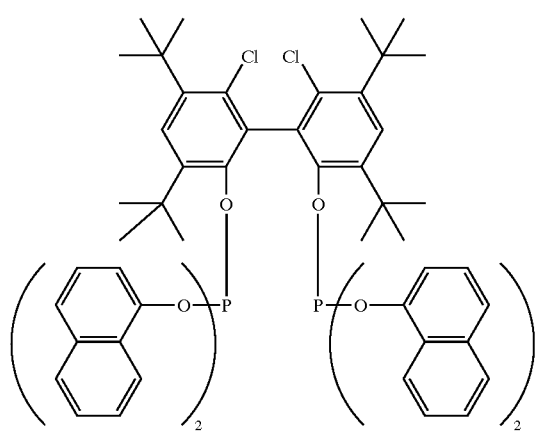
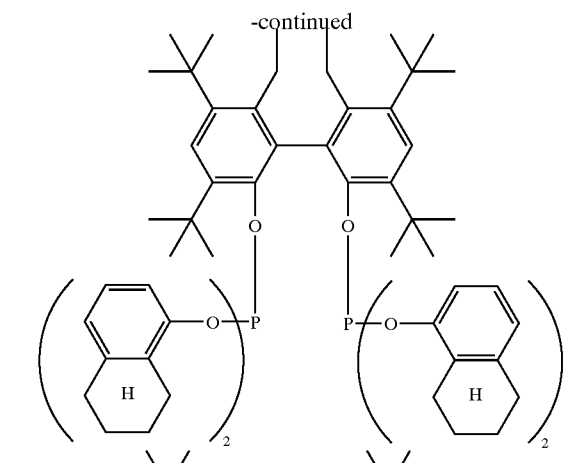
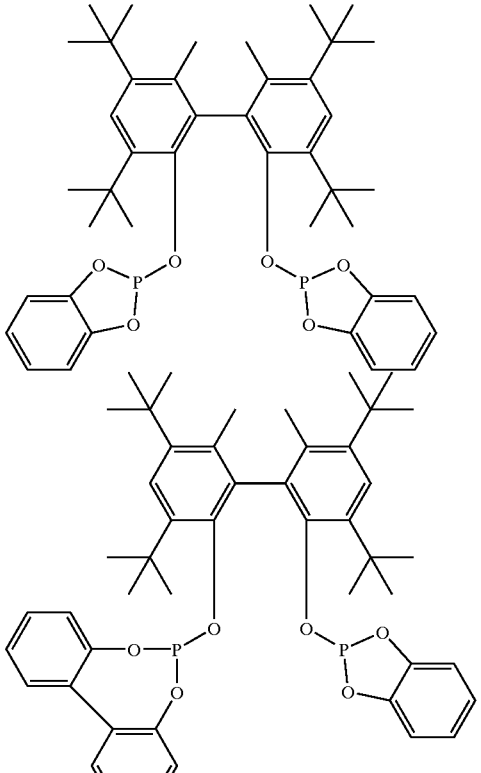
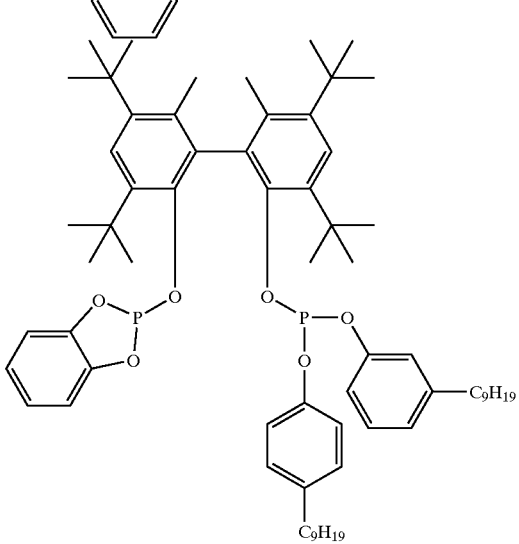

-continued

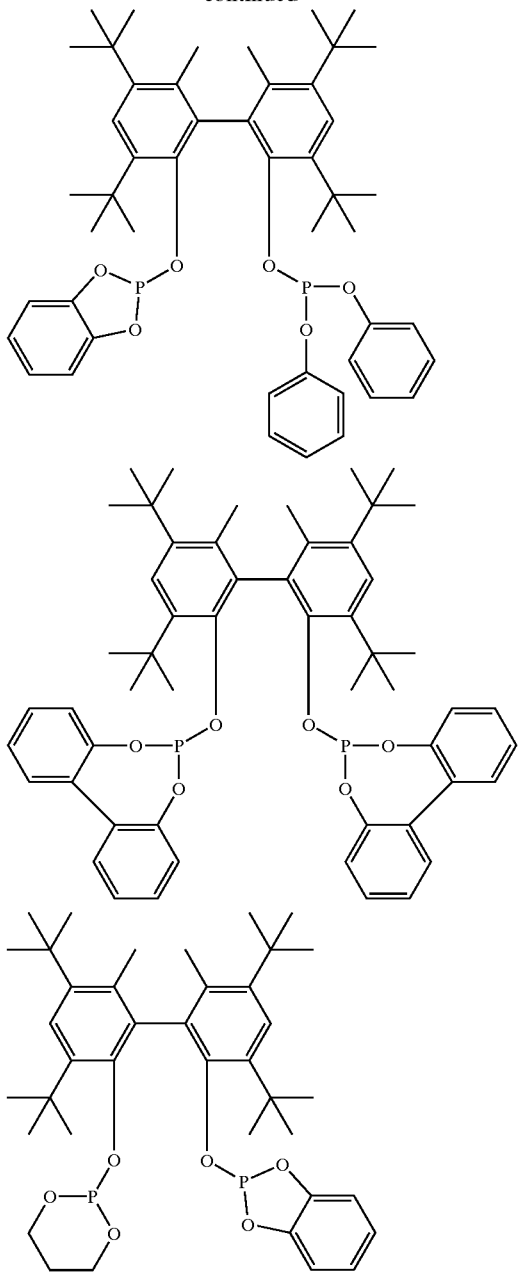

These phosphite ligands may be used individually or in combination. Mixed systems of monophosphites and bisphosphites or polyphosphites may be used, for example. The amount in which the phosphite compounds are used is not particularly limited, but the amount is preferably one affording the desired results for catalyst activity and selectivity. The range is generally about 0.1 to 500 mol, preferably 0.1 to 100 mol, and even more preferably 1 to 30 mol, per mol Group VIII noble metals.

The Group VIII noble metal compound used in the present invention may be a previously formed complex of a Group VIII noble metal compound and a phosphorus compound, or one produced in the reaction system from a precursor Group VIII noble metal compound and a phosphorus compound. Such a complex can be readily prepared by a common method from Group VIII noble metal compounds and phosphorus compounds. A desirable Group VIII noble metal compound is rhodium compound. Examples of rhodium compounds include inorganic or organic acid salts of rhodium such as rhodium chloride, rhodium nitrate, rhodium acetate, rhodium formate, sodium chlororhodate, and potassium chlororhodate; metallic rhodium supported on a carrier such as alumina, silica, or activated carbon; rhodium chelator compounds such as rhodium dicarbonyl acetylacetonate and rhodium (1,5-cyclooctadiene) acetylacetonate; and carbonyl complexes of rhodium such as tetrarhodium dodecacarbonyl, hexarhodium hexadecacarbonyl, $\mu,\mu'$-dichlororhodium tetracarbonyl, $\{Rh(OAc)(COD)\}2$ (where COD is 1,5-cyclooctadiene), and $\{Rh(\mu\text{-S-t-Bu})(CO)2\}2$. The amount in which Group VIII noble metal compounds are used is not particularly limited. Although the threshold is determined in consideration of the catalytic activity and selectivity, the concentration in the reaction zone, in terms of metal atoms, generally ranges from 0.05 mg to 5 g, preferably 0.5 mg to 1 g, and ideally 10 mg to 500 mg, relative to 1 liter reaction solvent.

Examples of olefin unsaturated compounds which can be used in the hydroformylation reaction, for example, in the present invention are not limited, provided that they are organic compounds having at least one olefinic double bond per molecule. Examples include olefinic compounds having a linear, branched, or cyclic structure, and internal or end unsaturated olefin compounds. Such olefins can contain 2 to 20 carbon atoms, preferably 2 to 8 carbon atoms, as well as groups or substituents such as carbonyl, carbonyloxy, oxy, hydroxy, oxycarbonyl, halogen, alkoxy, aryl, alkyl, and haloalkyl, which essentially have no effect on hydroformylation. Examples of olefin unsaturated compounds include α-olefin, internal olefins, alkyl alkenates, alkenyl alkanates, alkenylalkyl ethers, and alkenols.

Specific examples include olefins such as ethylene, propylene, butene, butadiene, pentene, hexene, hexadiene, octene, octadiene, nonene, decene, hexadecene, octadecene, eicosene, docosene, styrene, α-methylstyrene, cyclohexene, and propylene-butene mixtures, 1-butene-2-butene-isobutylene mixtures, 1-butene-2-butene-isobutylene-butadiene mixtures and other such lower olefin mixtures, propylene, n-butene, isobutylene and other such lower olefin dimers through tetramers and similar olefin oligomer isomeric mixtures; hydrocarbon olefins such as 3-phenyl-1-propene, 1,4-hexadiene, 1,7-octadiene, and 3-cyclohexyl-1-butene; and acrylonitrile, allyl alcohol, 1- hydroxy-2,7-octadiene, 3-hydroxy-1,7-octadiene, oleyl alcohol, 1-methoxy2,7-octadiene, methyl acrylate, methyl methacrylate, oleic acid methyl octa-1-ene-4-ol, vinyl acetate, allyl acetate, 3-butenyl acetate, allyl propionate, allyl acetate [sic], 3-butenyl acetate [sic], vinyl ethyl ether, vinyl methyl ether, allyl ethyl ether, n-propyl-7-octenoate, 3-butene nitrile, 5-hexeneamide, and other such polar group-substituted olefins. Any of these olefin unsaturated compounds can be used. More preferable are monoolefin unsaturated compounds having one olefinic double bond per molecule. Still more preferable are $C_2$ to $C_{20}$ hydrocarbon olefins. Ideal examples are propylene, or 1-butene, 2-butene, isobutene, and mixtures thereof, and 1-octene and octene mixtures.

The bisphosphite compounds are further-described, including methods of its preparation, in U.S. Pat. No. 5,910,600, the entire specification of which is incorporated by reference herein. The present invention may suitably employ any of the bisphosphite compounds disclosed and described in the aforementioned U.S. Pat. No. 5,910,600. It has been found that the above specified catalyst exhibits excellent catalytic activity and selectivity for the desired product while maintaining a high reaction rate.

The amount of ligand compound used to form the catalyst in the metal organophosphorus ligand complex catalyst suitably employed in the present invention is not particularly limited. Specifically, the amount of ligand compound used to form the in the metal organophosphorus ligand complex catalyst suitably employed in the present invention need only be that minimum amount necessary to provide the given ligand concentration desired to be employed and which will provide the basis for at least that amount which exhibits desirable catalytic activity and selectivity at the selected reaction temperature and pressure. In an illustrated preferred embodiment, the catalyst will exhibit a reaction half time of approximately one hour or less at the hydroformylation reaction temperature and pressure. For purposes of the present invention described herein, the term "reaction half time of one hour" as it is used to describe catalytic activity herein is intended to encompass the meaning that after the hydroformylation reaction has progressed for one hour, one half of the olefin remains. This particular given criteria is representative of the activity of the catalyst employed in the method of the present invention. In the specific illustrated embodiment where the ligand is selected to include bisphosphite compounds, the amount of the molar ratio of bisphosphite compound ligand to metal compound is in the range of approximately 0.1 to 500, preferably in the range of approximately 0.1 to 100, and more preferably in the range of approximately 1 to 30.

Although the amount of ligand compound, and independently and separately the amount of metal compound, used to form the metal organophosphorus ligand complex catalyst suitably employed in the present invention is not particularly limited and need be only be that minimum amount necessary to provide the given catalyst concentration desired to be employed and which will provide the basis for at least that amount which exhibits desirable catalytic activity and selectivity at the selected reaction temperature and pressure; it is preferred that for desirable catalytic activity to produce a desirable yield of aldehyde products with a high N/I ratio, the amount of organophosphorus ligand is to be greater than the amount of Group VIII metal in the catalyst composition.

In general, the hydroformylation reaction is carried out by reacting the olefin with a mixture of hydrogen ($H_2$) and carbon monoxide (CO) in the presence of the catalyst. The hydrogen and carbon monoxide are usually supplied as synthesis gas or "oxo gas." Typically, the oxo gas is supplied to the reactor in an equal molar ratio of approximately 1:1 $H_2$ to CO. Optionally, the oxo gas may be supplied to the reactor in a molar ratio in the range of approximately 100:1 to 1:10 $H_2$ to CO, and preferably in the range of approximately 10:1 to 1:10 $H_2$ to CO. The hydroformylation reaction is carried out for a given reaction time. The specific reaction time employed will vary and is dependent at least in part on many factors, such as but not limited to, the temperature, pressure, makeup and concentration of reactants, and the like.

As aforementioned, the method of the present invention may employ a solvent for the hydroformylation reaction. As described above, in the preferred embodiment, low boiling point solvents, such as aldehydes and/or alcohols, are employed as the solvent. However, it is to be understood that the invention is not limited to any particular type of solvent. Conventional solvents may be used with the present invention, and in this case temperature controlling means may be used to achieve the desired temperature range of the present invention. Thus, solvents finding suitable application in the present invention include conventional solvents used in the prior art such as aromatic hydrocarbons, which include toluene, xylene and dodecylbenzene. Other conventional solvents may be used including ketones such as acetone, diethyl ketone and methyl ethyl ketone; ethers such as tetrahydrofurane and dioxane; esters such as ethyl acetate and di-n-octyl-phthalate; high boilers produced as by-products during the hydroformylation reaction, such as condensation products of aldehyde; and the olefin. Thus the solvent is not limited; however, it is desirable to select the solvent such that the catalyst employed in the hydroformylation reaction is active, and preferably exhibits a reaction half time of approximately one hour or less when exposed to the solvent at the selected hydroformylation temperature and pressure.

The hydroformylation reaction may be carried out at a variety of pressures. The pressure range is suitably adapted to the system and will generally vary depending upon the type of catalyst and particularly the type of ligand employed and the reactor configuration topographies. For example, when employing a conventional metal organophosphorus ligand complex catalyst, the hydroformylation reaction may be carried out at a total gas pressure in the range of approximately 1 to 200 atm, preferably in the range of approximately 1 to 100 atm, with a range of approximately 3 to 50 atm being most preferred. When the ligand is in the form of a bisphosphite compound, the pressure of the hydroformylation reaction is carried out at pressure of of 1 atm or greater, with a range of 1 to 100 atm being suitable, this representing the total gas pressure within the system, and in an illustrative preferred embodiment of the present invention includes carrying out the hydroformylation reaction out at a total gas pressure in the range of approximately 3 to 50 atm.

Of particular advantage, the method of the present invention provides for operating at a relatively high aldehyde concentration in the reactor while preventing the large formation of high boilers. This is in great contrast to prior art methods, where a relatively high aldehyde concentration is unfavorable because it accelerates the formation of high boilers. More specifically, the method of producing aldehydes, comprising: reacting in a reaction mixture an olefinic compound with hydrogen and carbon monoxide in a hydroformylation in the presence of a catalyst, at a temperature of less than approximately 100° C., and the composition of said reaction mixture includes at least about 30 percent by weight of aldehyde product, wherein the formation of high boilers from the reaction are substantially minimized. Preferably, the composition of said reaction mixture includes aldehyde products in the range of about 35 to 99 weight percent, and more preferably in the range of about 50 to 95 weight percent.

Of particular advantage, the present invention provides a method of producing aldehydes wherein the degradation of the catalyst, and specifically the ligand compound of the catalyst is reduced. Specifically, experiments have shown the decomposition of the catalyst is reduced to a rate as low as 0.2 percent per hour (by weight). In fact, experiments show the method of the present invention enables achievement of a catalyst/ligand decomposition rate as low as 0.002 percent per hour at a reaction temperature of 70° C.

In the preferred embodiment described above, the method of the present invention allows the adaptation of a significantly simplified hydroformylation system wherein a number of expensive equipment units may be optionally reduced and/or eliminated. FIG. 2 shows a schematic diagram of one illustrated embodiment of a hydroformylation system which may be employed with the preferred embodiment of the present invention. In the preferred embodiment, the hydroformylation system 110 is comprised of simply a reactor 112 and an aldehyde removal distillation tower 114. Thus, the high boiler/catalyst removal system 18 in the prior art system of FIG. 1 and all of its variations, embodiment, types, modifications and complexities may be eliminated by the preferred method of the present invention. Alternatively, the hydroformylation system may be optionally equipped with all or part of the separation system units described in the prior art. Representative embodiments include employing a high boiler separation unit such as shown in FIG. 1 and described above, however, due to the reduction in formation of high boiling point by-product components according the present invention, such unit may be adaptively configured to the smaller load, thereby reducing its size and complexity. Of course, while the preferred embodiment is shown in FIG. 2 it is to be understood that the present invention is in no way limited to the illustrated preferred embodiment, and the method of the present invention may be practiced in prior art hydroformylation systems such as that depicted in FIG. 1, and optimally practiced in any heretofore known conventional hydroformylation systems. Preferably, the reactor 112 useful in the present invention is a well controlled plug flow reactor.

As described above, the temperature of the reaction is below approximately 100° C., and preferably below approximately 85° C., more preferably below about 80° $C_{-1}$ with a temperature in the range of approximately 45° C. to 70° C. being most preferred. To maintain this temperature range, the reactor may be suitably equipped with temperature controlling means such as water coolers known in the art. Representative temperature controlling means include a plurality of stages or coolers adaptively employed with the reactor 112. This arrangement is advantageous for providing substantially uniform temperature control through the volume of the reactor. Alternatively, other types of cooling equipment may be used, such as heat exchangers and the like. The particular type and size of the cooling equipment will be selected based on known heat exchange calculations and principles which are well known to those skilled in the art.

The hydroformylation reaction takes place in the reactor 112 and aldehyde products are optionally removed via a product outlet line 119. Gases may be purged out the top of the reactor 112 via purge line 120, and the oxo gas is optionally recycled back into the reactor 112. The aldehyde products are then conveyed to aldehyde removal distillation tower 114 shown in the representative illustration.

EXPERIMENTAL

A variety of experiments were performed to carry out the method of the present invention. The examples set forth below are provided for illustrative purposes only, and are not intended to limit the present invention in any way.

EXAMPLES 1 AND 2

Examples 1 and 2 demonstrate that NBD alone as a solvent can have a similar result as toluene (a conventional solvent). Using an autoclave representative of a semi-batch reactor, the hydroformylation of propylene to butyraldehyde was carried out in a number of experiments. Propylene was added and oxo gas was supplied to the autoclave reactor from a canister via a pressure controlled inlet line operatively attached to the autoclave reactor. The pressure and temperature of the autoclave reactor were maintained and the reaction was carried out in a semi-batch fashion. A table of the experimental conditions and results for two experiments are presented in Table 1:

TABLE 1

|  | Example 1 | Example 2 |
|---|---|---|
| Amt of PPY charged (g) | 4.4 | 4.6 |
| cat: Rh conc. (mg/l) | 80 | 80 |
| cat:Ligand to Rh ratio | 4.0 | 4.0 |
| solvent: type | Tol (60 ml) | NBD(60 ml) |
| $H_2$/CO molar ratio | 1:1 | 1:1 |
| temp. ° C. | 70 | 70 |
| total gas press (kg/cm$^2$G) | 9.0 | 8.5 |
| rxn time (hr) | 3.6 | 3.2 |
| cat. Rxn half time (min) | 22 | 29 |
| N/I ratio | 72 | 68 | where PPY is propylene, NBD is normal butyraldehyde, IBD is iso butyraldehyde, Tol is toluene, and HB is the high boilers.

In Example 1, a conventional solvent, in this case toluene (Tol) was used as the initial charged solvent. In Example 2 according to the present invention, an aldehyde, in this instance the normal butyraldehyde (NBD), is used as the initial charged solvent. The catalysts were prepared by using $[Rh(1,5\text{-cyclooctadiene})(\mu\text{-CH}_3\text{COO})]_2$ and the following ligand A to obtain the concentrations as shown in Table 1.

Ligand A

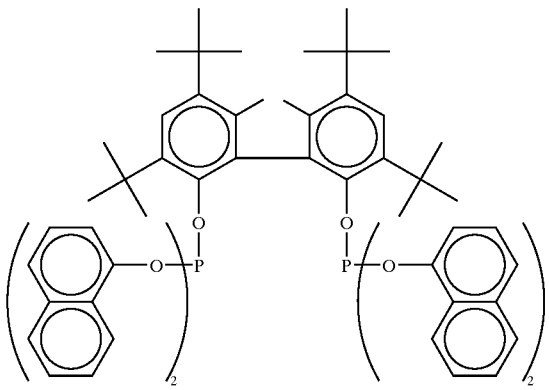

Each catalyst exhibited a reaction half time of less than one-half hour at the reported temperature and pressure. At the lower pressure of 8.5, the half time was greater at approximately 29 minutes.

EXAMPLES 3 TO 13

Experiments were conducted to evaluate the effect of temperature on the formation of high boilers. A solution of dissolved $[Rh(1,5\text{-cyclooctadiene})(\mu\text{-CH}_3\text{COO})]_2$ and ligand A, and treated with oxo gas, was used as a reaction solution. The results are set forth in Tables 2, 3 and 4 below. The designation of "Tol" in the Tables under solvent type represents an initial charge of toluene as the solvent in the reactions. NBD is added as a reactant in a ratio of approximately 1:1 in volume toluene to NBD. The designation of "NBD" in the Tables under solvent type represents an initial charge in the reaction of NBD alone as the solvent. The reaction was carried out in a reaction vessel. The reaction vessel was placed in an oil bath to suitable control the temperature. Samples were taken from the solution contained in the reaction vessel periodically over many hours. The composition of the samples were evaluated by gas chromatography (GC) to measure the amount of high boliers formed. The results and experimental conditions shown for similar reaction (rxn) times are depicted in Tables 2–5 below:

TABLE 2

|  | Example 3 | Example 4 |
|---|---|---|
| cat. Rh conc. (mg/l) | 500 | 250 |
| cat:Ligand to Rh ratio | 2.0 | 8.0 |
| solvent: type | Tol | Tol |
| temp. (° C.) | 130 | 130 |
| rxn time (hr) | 73 | 74 |
| Yield (mol percent) of Total HB: | 41 | 58 |

Examples 3 and 4 were conducted at temperatures of 130° C. After only about 73 hours, significant amounts of high boilers were formed. Example 5 was then run for another 17 hours to a total of 90 hours reaction time and compared to Example 6 carried out at 110 C and 137 hours, and Examples 7 and 8 both carried out at 70° C. and 116 and 145 hours, respectively. The results and experimental conditions are shown in Table 3 below:

TABLE 3

|  | Example 5 | Example 6 | Example 7 | Example 8 |
|---|---|---|---|---|
| cat. Rh conc. (mg/l) | 250 | 500 | 500 | 500 |
| cat:Ligand to Rh ratio | 8.0 | 2.0 | 4.0 | 4.0 |
| solvent: type | Tol | Tol | Tol | NBD |
| temp.(° C.) | 130 | 110 | 70 | 70 |
| rxn time (hr) | 90 | 137 | 116 | 145 |
| Yield (mol percent) of Total HB: | 72 | 31 | 1.2 | 1.6 |

As illustrated in Table 3, significant amounts of high boilers are formed at the higher temperatures of 110 and 130° C. At the lower temperatures, particularly at 70 C, minimal amounts of high boilers are formed even at longer reaction times. Examples 9, 10 and 11 were then further carried out for another total of 167, 359 and 359 hours, respectively with Example 9 being carried out at the higher temperature of 110° C. The results and experimental conditions are shown in Table 4 below:

TABLE 4

|  | Example 9 | Example 10 | Example 11 |
|---|---|---|---|
| cat. Rh conc. (mg/l) | 500 | 500 | 500 |
| cat:Ligand to Rh ratio | 2.0 | 4.0 | 4.0 |
| solvent: type | Tol | Tol | NBD |
| temp. (° C.) | 110 | 70 | 70 |
| rxn time (hr) | 167 | 359 | 359 |
| Yield (mol percent) of Total HB: | 37 | 9.2 | 3.8 |

Finally, Examples 12 and 13 were further run to a total of approximately 1100 and 1120 hours, respectively at the lower temperature of 70° C. The experimental results and conditions are shown in Table 5:

TABLE 5

|  | Example 12 | Example 13 |
|---|---|---|
| cat. Rh conc. (mg/l) | 500 | 500 |
| cat:Ligand to Rh ratio | 4.0 | 4.0 |
| solvent: type | Tol | NBD |

TABLE 5-continued

|  | Example 12 | Example 13 |
|---|---|---|
| temp. (° C.) | 70 | 70 |
| rxn time (hr) | 1100 | 1120 |
| Yield (mol percent) of Total HB: | 19 | 24 |

The experiments were conducted with relatively high catalyst concentrations to simulate the accelerate the accumulation of high boilers that would be experienced in normal prolonged operation in an actual hydroformylation facility. As shown in Tables 2 to 5, the formation of high boilers is reduced dramatically with a reduction in the reaction temperature. Specifically, as shown in Examples 3 and 4, at 130° C. the yield of high boilers are very high after only approximately 73 hours. Whereas at 70° C. as shown in Example 12 and 13 in Table 5, the high boilers yield is significantly reduced; about 19 mol percent after more than 1000 hours, and less than 25 mol percent after more than 1100 hours, respectively. Applying these results (for example 19 mol percent HB, over 1100 hrs at 8 times the typical reaction rate) to a hydroformylation production facility shows that said facility can operate for approximately one year without forming a detrimental concentration of high boilers according to the method of the present invention. These numbers correspond to a yield of approximately 0.1% of the olefinic compound (in this case propylene), which is a very significant reduction in the formula of high boilers.

EXPERIMENTS 14 TO 18

A number of experiments were conducted to show the reduction in catalyst degradation, and in particular the reduction in the ligand degradation, by employing a low temperature in the hydroformylation reaction according to the method of the present invention. A solution of dissolved [Rh(1,5-cyclooctadiene)($\mu$-CH$_3$COO)]$_2$ and ligand A, and treated with oxo gas, was used as a reaction solution. The designation of "Tol" in the Tables under solvent type represents an initial charge of toluene as the solvent in the reaction. NBD is added as a reactant in a ratio of approximately 1:1 in volume toluene to NBD. The designation of "NBD" in the Tables under solvent type represents an initial charge in the reaction of NBD alone as the solvent. The reaction was carried out in a reaction vessel. The reaction vessel was placed in an oil bath to suitable control the temperature. Samples were taken from the solution contained in the reaction vessel periodically over many hours. The composition of the samples were evaluated by gas chromatography (GC) to measure the amount of high boilers formed. Experiments 14 to 18 were conducted with the same equipment and procedure as hereto described in Experiments 3 to 13. Samples were taken periodically and tested using LC techniques to determine the amount of ligand decomposition that had occurred. The experimental conditions and results are shown in Table 6 below:

TABLE 6

|  | Ex 14 | Ex 15 | Ex 16 | Ex 17 | Ex 18 |
|---|---|---|---|---|---|
| cat. Rh conc. (mg/l) | 500 | 500 | 500 | 500 | 500 |
| cat:Ligand to Rh ratio | 2.0 | 4.0 | 2.0 | 4.0 | 4.0 |
| solvent: type | Tol | Tol | Tol | Tol | NBD |

TABLE 6-continued

|  | Ex 14 | Ex 15 | Ex 16 | Ex 17 | Ex 18 |
| --- | --- | --- | --- | --- | --- |
| temp. (° C.) | 150 | 130 | 110 | 70 | 70 |
| rxn time (hr) | 9.0 | 89 | 167 | 1100 | 1120 |
| decomposition rate (%/hr) | 8.0 | 1.6 | 0.06 | 0.002 | 0.002 |

In all of the examples the catalysts were prepared by using [Rh(1,5-cyclooctadiene)($\mu$-CH$_3$COO)]$_2$ and the following ligand A to obtain the concentrations as shown in Table 6.

Ligand A

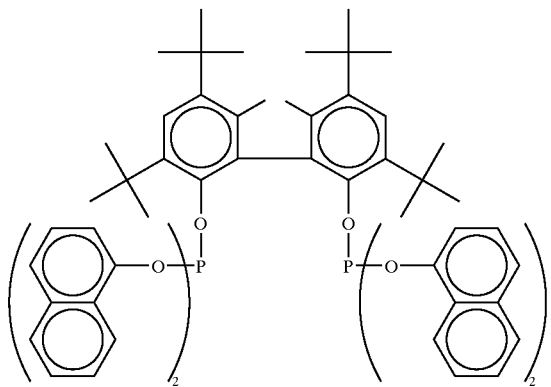

As shown, the method of the present invention illustrated in examples 17 and 18 significantly reduce the decomposition rate of the catalyst to a value of 0.002 percent per hour as compares to the significantly higher decomposition rate exhibited by the higher temperature processes of Examples 14, 15 and 16. Examples 1–18 were conducted to confirm both the reduction of producing high boilers and degradation of ligands in the reaction according to the method of the present invention. Examples 19 and 20 below describe experiments which confirm effects of the concentration of catalyst solution in the distillation tower as representative examples of the downstream catalyst process path.

EXAMPLES 19 AND 20

Examples 19 and 20 demonstrate the effects on catalyst degradation and high boiler formation in the downstream catalyst process path. Specifically, in Examples 19 and 20 the downstream catalyst process path is represented by the distillation process. The distillation towers in both examples are at atmospheric pressure. In Example 19, distillation at 130° C. (toluene/C$_{18}$ or higher aldehyde condensate mixed solvent) was performed. Distillation at this high temperature is representative of the prior art systems. Specifically, to toluene and C$_{18}$, or higher aldehyde condensate mixed solvent (weight ratio 6:4), was added and dissolved, in a nitrogen atmosphere, a Rh(acac)(CO)$_2$ complex, resulting in a Rh concentration of 125 mg/l, with a ligand (used in Example 1) molar ratio of 4-fold that of the Rh. The resulting solution (291 ml) was transferred to a 500 ml vertically stirred autoclave, and 19.6 g propylene (about 6.7 g propylene used per 100 ml reaction solution) was added. The contents were held at a temperature of about 70° C. while stirred. Oxo gas was introduced, resulting in a pressure of 5 kg/cm$^2$G in the autoclave, and an oxo reaction was brought about for 2.5 hours as the pressure was maintained.

The autoclave was cooled, and the reaction solution was transferred under nitrogen to a round-bottomed flask with a cooling tube for distillation. The contents were heated to a liquid temperature of 130° C. over about 50 minutes at ordinary pressure, and the temperature was maintained for 1 hour. The butyraldehyde that was meanwhile produced was distilled off. The internal pressure was then brought to 70 mm Hg as the temperature was maintained, and the toluene was distilled off. Analysis of the ligand in the residue by liquid chromatography revealed that 0.8 percent of the ligand had decomposed.

Toluene and ligand in the amount that had been decomposed were added to the residue, the catalyst concentration was restored to the initial level, and the preceding reaction and distillation were repeated twice. The result was that 2.3 percent of the ligand used had decomposed.

To demonstrate the effects of temperature, Example 20 was conducted with distillation at 77° C. in accordance with the present invention. In this example the lower temperature is achieved by using NBD as the solvent. However, as described above, other means may be used to achieve the desired temperatures. Specifically, to n-butyraldehyde was added and dissolved, in a nitrogen atmosphere, a Rh(acac)(CO)$_2$ complex, resulting in a Rh concentration of 125 mg/l, with a ligand (used in Example 1) molar ratio 4-fold that of the Rh. The resulting solution (313 ml) was transferred to a 500 ml vertically stirred autoclave, and 20.0 g propylene (about 6.7 g propylene used per 100 ml reaction solution) was added. The contents were held at a temperature of about 70° C. while stirred. Oxo gas was introduced, resulting in a pressure of 5 kg/cm$^2$G in the autoclave, and an oxo reaction was brought about for 2.5 hours as the pressure was maintained.

The autoclave was cooled, and the reaction solution was transferred under nitrogen to a round-bottomed flask with a cooling tube for distillation. The contents were heated to a liquid temperature of 77° C., the lid on the distillation side was closed when the equivalent of the amount of aldehyde produced had been reached (10 percent of the liquid), and the contents were heated to reflux for 2 hours. The contents were then cooled, and analysis of the ligand in the residue by liquid chromatography revealed that 0.3 percent of the ligand had decomposed, which is a significant reduction compared to the decomposition in example 19.

Ligand in the amount that had been decomposed was added to the residue, the catalyst concentration was restored to the initial level, and the preceding operations were repeated twice. The result was that 0.7 percent of the ligand used had decomposed. Examples 19 and 20 demonstrate the significance of temperature in the downstream catalyst process path and the significant advantage achieved by the method of the present invention.

As taught by the foregoing description and examples, a greatly advanced method of producing aldehydes is provided by the method of the present invention. The foregoing description of specific embodiments and examples of the invention have been presented for the purpose of illustration and description, and although the invention has been illustrated by certain of the preceding examples, it is not to be construed as being limited thereby. They are not intended to be exhaustive or to limit the invention to the precise forms disclosed, and obviously many modifications, embodiments, and variations are possible in light of the above teaching. It is intended that the scope of the invention encompass the generic area as herein disclosed, and by the claims appended hereto and their equivalents.

We claim:

1. A method of producing aldehydes in a hydroformylation system which includes a reactor and a downstream catalyst process path, comprising reacting an olefinic compound with hydrogen and carbon monoxide in a hydroformylation reaction and in the presence of a catalyst, at a temperature in the reactor and downstream catalyst process path of less than approximately 80° C., such that formation of high boiling point by-products components from the reaction are limited to a yield of less than approximately 2 percent by weight of the olefinic compounds and the decomposition rate of the catalyst is not greater than approximately 0.2 weight percent per hour, in the downstream catalyst process path.

2. The method of claim 1 wherein decomposition of a ligand compound of said catalyst during the reaction and in the downstream catalyst process path is substantially minimized.

3. The method of claim 1 wherein the temperature in the reactor is in the range of approximately 45 to 70° C., and the temperature in the downstream catalyst process path is in the range of approximately 40 to 80° C.

4. The method of claim 1 wherein said catalyst is selected such that said catalyst exhibits a reaction half time of one hour or less at a selected temperature and pressure.

5. The method of claim 1 wherein said catalyst is comprised of a metal-organophosphorus ligand complex catalyst.

6. The method of claim 1 wherein said catalyst comprises a compound selected from Group VIII of the Periodic Table, and having a phosphite compound as a ligand.

7. The method of claim 1 wherein said catalyst includes a Rh compound, and having a bisphosphite compound as a ligand.

8. The method of claim 6 wherein said phosphite compound has the following formula:

   (1)

wherein R1, R2, and R3 are optionally C1 to C30 substituent-bearing alkyl groups, cycloalkyl groups, aryl groups, aralkyl groups, and heteroaryl groups.

9. The method of claim 8 which at least one of R1, R2, or R3 in General Formula 1 is independently a substituted aryl group represented by:

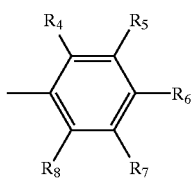

wherein R4 is —C(R9)(R10)R11 or an optionally substituted aryl group; R9, R10, and R11 are each independently a hydrogen atom, fluorohydrocarbon group or hydrocarbon group; R4 has steric hindrance as a whole equal to or greater than isopropyl groups; and R5, R6, R7, and R8 are each independently a hydrogen atom or organic group, or condensed aromatic rings or hetero rings with adjacent substituents.

10. The method of claim 6 wherein said phosphite compound has the following formula:

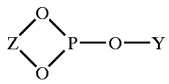   (3)

wherein Z is a divalent organic group, and Y is an optionally substituted monovalent organic group.

11. The method of claim 6 wherein said phosphite compound has the following formula:

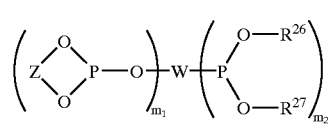   (9)

wherein Z is a divalent organic group; R26 and R27 are each independently optionally C1 to C30 substituent-bearing alkyl groups cycloalky groups, aryl groups, aralkyl groups, and heteroaryl groups; W is an optionally substituted m-valent hydrocarbon group; and m1 and m2 are each independently integers 0 to 6, where m=m1+m2 has a value of 2 to 6.

12. The method of claim 11 in which W in General Formula 9 is represented by the following formula:

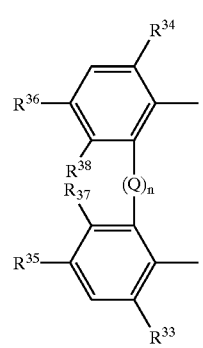   (10)

wherein R37 and R38 are each independently a $C_1$ to $C_{12}$ alkyl group, cycloalkyl group, alkoxy group, silyl group, siloxy group, or a halogen atom or hydrogen atom; R33 through R36 are each independently a $C_1$ to $C_{20}$ alkyl, cycloalkyl, alkoxy, silyl, or siloxy group, or a halogen or hydrogen atom; in which R35 and R37 and/or R36 and R38 each independently bond to each other to form part of a cyclic structure consisting of 3 to 40 carbons; Q is a divalent bridge group selected from the group comprising of —CR15R16—, —O—, —S—, —NR17—, —SiR18R19—, and —CO—, where R15 and R16 are each independently selected from the group comprising of hydrogen, $C_1$ to $C_{12}$ alkly groups, phenyl, tolyl, and anisyl; and R17, R18, and R19 are each independently a hydrogen or methyl group; and n is 0 or 1.

13. The method of claim 6 wherein said phosphite compound is selected from the group of
{2-[2-(di(2-naphthyloxy)phosphinoxy)-3,5-bis(tert-butyl)phenyl]-4,6-bis(tert-butyl)phenoxy}di(2-naphthyloxy)phosphine,
{2-[2-(di(2-naphthyloxy)phosphinoxy)-3,5-bis(tert-butyl)-6-methylphenyl]-4,6-bis(tert-butyl)-3-methylphenoxy}di(2-naphthyloxy)phosphine,
{4,6-bis(tert-butyl)-2-[3,5-bis(tert-butyl)-2-(dinapthyloxyphosphinoxy)phenyl]phenoxy}dinaphthyloxyphosphine, {4,6-bis(tert-butyl)-2-[3,5-bis(tert-butyl)-2-(dinapthyloxyphosphinoxy)-6-methylphenyl]-3-methylphenoxy}dinaphthyloxyphosphine, {6-(tert-butyl)-2-[3-(tert-butyl)-2-(dinapthyloxyphosphinoxy)-5-methoxy-6-methylphenyl]-4-methoxy-3-methylphenoxy}dinaphthyloxyphosphine, 6-{6-(tert-butyl)-2-[3-(tert-butyl)-2-dibenzo[d,f]1,3,2-dioxaphosphin-6-yloxy-5-methoxyphenyl]-4-methoxyphenoxy}dibenzo[d,f]1,3,2-dioxaphosphine, 6-{4,6-bis(tert-butyl)-2-[3,5-bis(tert-butyl)-2-bibenzo[d,f]1,3,2-dioxaphospin-6-yloxyphenyl]phenoxy}dibenzo[d,f]1,3,2-dioxaphosphine, and 6-{4,6-bis(tert-butyl)-2-[3,5-bis(tert-butyl)-6-dibenzo[d,f]1,3,2-dioxaphospin-6-yloxy-2-methylphenyl]-3-methylphenoxy}dibenzo[d,f]1,3,2-dioxaphosphine.

14. The method of claim 1 further comprising operating the reaction at a pressure in the range of approximately 1 to 200 atm.

15. The method of claim 1 further comprising operating the reaction at a pressure in the range of approximately 1 to 100 atm.

16. The method of claim 1 further comprising providing a solvent to the reactor, wherein said solvent exhibits a boiling point equal to or greater than the boiling point of said aldehydes at an operational pressure of the hydroformylation system.

17. The method of claim 16 wherein said solvent exhibits a boiling point of equal to or less than 100° C. at an operational pressure of the hydroformylation system.

18. The method of claim 1 wherein the yield of said high boiling point by-product components is less than approximately 1 percent of the olefinic compound.

19. The method of claim 1 wherein decomposition of a ligand compound of said catalyst during the reaction is substantially minimized at a rate of equal to or less than 0.02 weight percent per hour.

20. A method of producing aldehydes comprising the steps of:
reacting an olefinic compound with hydrogen and carbon monoxide at a temperature in the range of approximately 45 to 70° C. in a hydroformylation reaction in a reaction mixture containing a catalyst to produce said aldehydes; and
separating said aldehydes from said reaction mixture at a temperature in the range of approximately 40 to 80° C.;
wherein said catalyst does not undergo substantial deactivation during the hydroformylation reaction or during said separation step and said deactivation is not greater than a rate of approximately 0.2 weight percent per hour of operation of said hydroformylation reaction and wherein the formation of high boiling point by-product components are limited to a yield of less than approximately 2 percent by weight of the olefinic compound.

21. A method of producing aldehydes in a hydroformylation system which includes a reactor and a downstream catalyst process path, comprising the steps of:
reacting an olefinic compound with hydrogen and carbon monoxide in a hydroformylation reaction mixture containing a catalyst, at a temperature in the reactor and downstream catalyst process path of less than approximately 80° C., to produce a reaction solution including one or more aldehyde products and high boiling point by-product components;
separating said aldehydes from said reaction mixture; and
providing a solvent as a starting material to the reaction, the solvent being comprised, at least partially, of one or more aldehyde,
such that formation of high boiling point by-product components from the reaction, and decomposition of the catalyst, are substantially minimized.

22. The method of claim 21 wherein the step of providing a solvent as a starting material further comprises recycling the one or more aldehyde products to the reaction.

23. The method of claim 21 wherein said solvent is comprised substantially of a mixture of said one or more aldehydes, or the one or more aldehyde products, and said high boiling point by-product components.

24. The method of claim 21 wherein said aldehydes and optionally said aldehyde products, include normal and iso aldehydes, and wherein said solvent is comprised substantially of said normal aldehydes.

25. The method of claim 21 wherein said solvent is comprised substantially of a mixture of said one or more aldehydes, and of a compound selected from the group consisting of aromatic hydrocarbons, ketones, ethers, esters and the olefinic starting material, and any combination thereof.

26. The method of claim 24 wherein said solvent has a composition of approximately 50 percent or greater by weight of said aldehyde products.

27. The method of claim 21 wherein said reaction solution is comprised of alcohol products and the solvent is comprised, at least partially, of said alcohol products.

28. The method of claim 26 wherein said solvent is comprised substantially of any one of said aldehydes, said aldehyde products, said alcohol products, said high boiling point by-product components, and any mixtures thereof.

29. The method of claim 21 wherein said hydroformylation reaction and the downstream catalyst process path is carried out at a temperature of less than approximately 85° C.

30. The method of claim 20 wherein said aldehydes are n-butyraldehyde and iso-butyraldehyde.

* * * * *